United States Patent [19]
Choi et al.

[11] Patent Number: 5,866,405
[45] Date of Patent: Feb. 2, 1999

[54] GENETICALLY ENGINEERED TRANSMISSIBLE HYPOVIRULENCE

[75] Inventors: Gil Ho Choi, Glen Ridge; Donald Lee Nuss, Passaic, both of N.J.

[73] Assignee: University of Maryland Biotechnology Institute, Baltimore, Md.

[21] Appl. No.: 459,146

[22] Filed: Jun. 2, 1995

Related U.S. Application Data

[63] Continuation of Ser. No. 832,117, Feb. 6, 1992.

[51] Int. Cl.$^6$ ........................................................ C12N 1/13
[52] U.S. Cl. .................................. 435/254.11; 435/320.1; 536/23.74
[58] Field of Search ................................ 424/93.21, 93.5; 435/254.11, 172.3, 320.1; 536/23.74

[56] References Cited

PUBLICATIONS

Turchetti, et al. Bulletin OEPP/EPPO, 18, pp. 67–72 (1988).
Turchetti, et al. Eur. J. For. Path, 21 pp. 65–70 (1991).
Anagnostakis, Forest Science, 36, No. 1 pp. 113–124 (1990).
Shapira, et al. EMBO, J. 10, vol. 4, pp. 731–739 (1991).
Choi & Nuss, EMBO, J. 11: No. 2 pp. 473–477 (1992).
Choi et al. PNAS (USA) 88: pp. 1167–1171 (1991).
Choi et al. Virology 183: pp. 747–752 (1991).
Shapira et al.J. of Biolog.Chem.266, No.29, pp. 19419–19425 (1991).
Koonin et al. Proc.Natl.Acad.Sci. USA 88:pp. 10647–10651 (1991).
Nuss, et al. Annu.Rev.Phytophathol 28 pp. 37–58 (1990).
Shapira et al. The EMBO J. 10:No.4 pp. 741–746 (1991).
Van Alfen, Annu.Rev.Phytophathol 20 pp. 349–362 (1982).
Rae et al. EMBO J. 8, pp. 657–663 (1989).

*Primary Examiner*—James Ketter
*Attorney, Agent, or Firm*—Steven J. Hultquist; William A. Barrett

[57] ABSTRACT

Fungi and fungal spores which are modified to confer a transmissible hypovirulent phenotype, related polynucleotides, and use of these fungi to control fungal diseases.

24 Claims, 23 Drawing Sheets

FIG. 1A

```
CCGGAGAAAGTGATTTGCTTTCTTCCATGAGGCTCCCT                                          120
GAGGCCCTTGTAGTAACCTCTCCCCGCTGCCGTGAGCGA                                         240
TGAAAACGGATGTACCATCTAGCTGTGGAGTAGTGACC                                          360
CGGTCTCTTAAGAGTTCATTGGTACGGTTGACCCCGAA                                          480
ATCCTTTCGTCAGCGTGAGGACGGAAGAGGTGGTCCCT                                          600
 D  P  F  V  S  V  R  T  E  E  V  V  P                                          35
TGCGCACCCCTGACGGGTATGTAAGTGCCAGGTCCAC                                           720
 L  R  T  P  D  G  V  C  K  C  Q  V  H                                          75
GGCCTCGCCGGTGTTCCTTGGAACAACTACGAAGGAG                                           840
 R  P  R  R  C  S  L  E  Q  R  T  K  E                                          115
TTCGAGGCCTGTGCTCATCTCGGAACGGTTCCCTTGCT                                          960
 V  R  G  L  C  S  S  R  N  G  S  L  A                                          155
TACGTGTGGCAGACTATCTTAGGCTGCTACAATGGGTT                                          1080
 V  R  V  A  D  Y  L  R  L  L  Q  W  V                                          195
AGTCTGAGCAGGATGGGCCCTTTTCTACCAAGCCATT                                           1200
 Q  S  E  Q  D  G  A  L  F  Y  Q  A  I                                          235
CCCTTAGGGTTGAACCTGTGACTCCACAGGTTACCCGC                                          1320
 A  L  R  V  E  P  V  T  P  Q  V  T  R                                          275
AGGATGCTCTTGTGCTACGGAGTTGAGGAACGTCAAT                                           1440
 Q  D  A  L  V  A  T  E  L  R  N  V  N                                          315
CCGAACTCCTCAAGTTCGATGCGCCCTTCGGTCGCGC                                           1560
 A  E  L  L  K  F  D  A  R  L  R  S  R                                          355
TGCCACAACGCCTTGCTGGTCTCTCCAAACAAGGCCGT                                          1680
 L  P  Q  R  L  A  G  L  S  K  Q  G  R                                          395
TCGTCCATAACTGGAAGGATTCCGCTGCCCTGGCAGTG                                          1800
 V  V  H  N  W  K  D  S  A  A  L  A  V                                          435
ATGTCGTTGCTTCCATTTCGGAAGCAATTGAAACCACT                                          1920
 N  V  A  S  I  S  E  A  I  E  T  T                                             475
```

FIG.1B

```
CTACGGCGGAATAAACCCGCTTTGCCTTGGATGGTCTTCATCTGCCATTGTCACGACCCGGTTGAGGTCGT
 L  R  R  N  K  T  R  F  A  L  D  G  L  H  L  A  A  S  A  I  V  T  T  R  L  R  S
AAATCAACCACTTCCTGGATATGGAGGCATGTGCCTTCATCAATCCAGGACGCCCTGAACCTGACTTCGTCAGGACAAGC
 K  S  T  T  S  W  I  W  R  H  V  P  S  S  I  Q  D  A  L  N  L  T  S  V  R  D  K
GTTGCGCAGGGCATGTCCGACTTCCGGAGGGCAAAGCGGGCATTGGCGTCGCCAAGCCCGTAATCGGAACATCCGTG
 V  A  Q  G  M  S  D  F  R  R  A  K  R  A  L  A  I  V  A  K  P  V  I  R  N  I  R

CTTCGCCATTCTCGCGACGCATTTAATAAGAAGCTGCGTACAAAGGCTGCCGTGGCCACGAAGGTCCACAAATAAATTT
 L  R  H  S  R  D  A  F  N  K  K  L  R  T  K  A  V  A  A  T  K  V  H  K  I  K  F  #
RTQVMDGPTWTALSESCRDLFFASGEG
GAACACAGGTCATGGACGGGCCAACATGGACTGCCCTTTCGTGTGAGTCGTGCAGGACAGGTTGTCTTTGCATCCGGGAAGG
SYTKIRLFRSGRFEVSVDGKSFGQGNR
CGTACACCAAGATACGCTTATTTCGCAGCCGGTGTCCGGTTCGAGGTGTCGGTTGACGGAAAGAGTTTTGGCCAGGCGCAACCG
TPFGYPAEDKEIALQDYNHKQLLGEMFL
ACCCTTTTGGATATCCTGCCGAGGACAAGGAAATAGCGCTTCAGGATTACAATCACAAGCAGTTGCTGGGTGAGATGTTCTT
 A  E  F  F  R  Y  V  D  D  L  K  W  D  V  G  V  F  R  D  R  R  S  L  T  E  L  H
CTGAGGCTTTCTTTCGTTACGTTGACGACCTGAAATGGGATGTCGGGGATGTCCGTGACCGTCGCTAACGGAACTTCA
 S  V  A  K  L  E  W  P  P  L  P  I  I  Q  A  P  T  I  L  A  G  I  I  D  N  F  K
CGGTGGCCAAACTCGAATGGCCCACTATCATCCAGGCCCGACAATACTAGCCGGTATCATCGACAATCATTGAACTTCAA
 Q  G  L  S  W  T  R  Y  D  G  D  A  S  V  P  T  S  L  L  S  N  R  Q  H  A  R  F  W
AAGGGTTGTCATGGACCAGATACGATGGCCAAGTCGCGAAAATCTCGACAGCACCACGCGAGGTTCTG
 K  E  G  F  I  K  L  W  A  Q  K  S  R  K  W  Q  D  H  M  A  R  S  I  G  L  S  H  E
AGGAAGGCTTCATCAAGCTCTGGGCCCAGAAATCTCGGCAAGTGGCAGGACCACATGGCGAGATCGATAGGATTAAGTCACGA
 E  A  K  P  H  L  V  P  M  E  E  A  K  E  A  P  R  Q  Q  L  V  P  R  S  T  F  V
AAGCAAAGCCCCATCGTCCCCATGGAAGAGGCGAAAGAGGCACCTAGGCAGCAGCTTGTTCCTAGGCGTTCAACTTTCGT
 R  V  P  V  E  E  G  R  C  F  F  L  F  N  N  Q  V  T  P  A  I  F  D  K  K  P  L
GGGTGCCGGTCGAAGAGAGGTCGATGTTTCGAGCTCTTGTTCAATAATCAAGTAACCCCTGCAATTTCGACAAGAAGCCATT
 C  T  M  D  S  L  E  I  S  H  S  D  Q  C  V  H  I  V  A  G  E  T  F  R  N  Y  D  E
```

FIG.1C

```
GGAACCAAGAGGAAATTCGTGCTGTCGCGAATTTCGT  2040
 W  N  Q  E  E  I  R  A  G  R  E  F  R    515
TCGACCCCGGCCGCCGGTTTGGTTACGTGCAGGCTGCG  2160
 L  D  P  G  R  A  F  G  Y  V  Q  A  A    555
ACCCCTATGAGCACGGGTTTGTCAAGCGAGATGGTAAG  2280
 D  P  Y  E  H  G  F  V  K  R  D  G  K    595
                                            12
AATGTATAAGGAAGCCGAACGACCTATTGAAGTGTGGC  2400
622
 M  Y  K  E  A  E  R  P  I  E  V  W          52
                                           2520
 G  E  H  M  T  L  D  I  I  Q  P  D
TGGTGAGCACATGACGCTCGATATCATCCAGCCTGATT
 Y  R  F  V  F  R  Y  D  S  L  L  S          92
TTATAGATTCGTCTTTCGCTATGACTCTTTGCTGTCGA  2640
 K  L  P  D  S  Y  V  D  G  R  P  I         132
GAAGCTTCCTGACTCCTATGTTGACGGGAGACCGATCG  2760
 L  P  A  S  S  G  L  T  T  A  Q  V         172
TTTACCAGCATCATCTGGTTTAACAACTGCACAAGTTT  2880
 I  C  F  P  V  N  G  K  W  I  Y  G         212
GATTTGCTTCCCCGTAAACGGGAAATGGATCTATGGTC  3000
 N  E  K  D  I  P  T  G  L  K  L  S         252
GAACGAGAAGGACATCCCCACCGGCCTGAAGCTTTCAA  3120
 A  A  V  E  L  V  R  A  T  R  V  N         292
GGCCGCTGTAGAGTTGGTTCGTGCAACAAGAGTGAACG  3240
 D  N  H  E  E  V  E  I  D  T  L             332
CGATAACCATGAGGAGGTTGAGATTGACACCCTTC     3360
 L  K  D  V  L  G  V  F  E  E  N  V         372
GCTTAAAGACGTCCTCGGCGTGTTCGAAGAGAATGTCT  3480
 I  K  A  V  L  E  V  I  L  E  N  E         412
```

```
AATCAAAGCCGTTCTCGAGGTCATTCTTGAGAACGAGC            3600
 W  V  R  N  G  L  K  L  A  K  G  L              452
GTGGGTCAGAAATGGGCTCAAGCTAGCGAAGGGTCTAG            3720
 D  N  G  Q  P  L  P  G  R  S  D  Q              492
TGACAACGGACAGCCCCTCCCGGGCAGGTCCGACCAAT            3840
 G  L  P  G  D  F  L  S  N  Y  P  R              532
TGGGCTACCTGGGGATTTCTTGTCGAATTACCCTAGAC            3960
 C  S  P  V  L  N  V  T  A  N  A  D              572
TTGTTCACCGGTGCTCAACGTGACTGCTAATGCAGACT            4080
 D  I  L  V  P  C  R  G  I  A  T  R              612
TGACATCCTCGTTCCTTGCAGGGCATCGCAAACCCGAA            4200
 D  N  Y  G  W  P  V  F  N  P  V  I              652
TGACAATTATGGTTGGCCAGTGTTCAATCCGGTCATCC            4320
 Y  D  A  L  E  Y  L  V  H  T  A  T              692
GTATGACGCACTAGAGTATCTAGTGCACACTGCGACGG            4440
 P  F  G  S  W  C  K  N  Y  K  F  E              732
TCCTTTCGGCTCGTGGTGCAAGAACTACAAGTTCGAAG            4560
 K  T  C  R  R  N  P  P  E  E  N  L              772
AAAAACCTGTCGCCGCAACCCCCGAAGAAAAACTTGC             4680
 V  P  L  Y  F  T  L  Y  V  P  Y  L              812
AGTGCCATTATACTTCACACTCTATGTGCCGTACCTGC            4800
 Y  A  C  D  A  W  C  R  L  F  F  F              852
CTACGCGTGTGACGCCCTGGTGCCGTTTATTTTTCTTCG           4920
 M  G  T  R  G  D  H  V  P  P  R  F              892
AATGGGAACAAGAGGAGATCACGTGCCACCACGGTTCT            5040
 K  K  G  K  L  G  S  L  L  P  G  Y              932
CAAGAAAGGGAAGCTCGGAAGCTTGTTGCCAGGCTATC            5160
 Y  N  L  A  P  P  R  S  Y  I  N  K              972
```

```
GTACAACTTAGCACCGCCTCGCAGCTACATCAACAAGA  5280
 T  F  W  P  D  W  Q  I  G  C  L  R       1012
CACGTTCTGGCCCGACTGGCAAATTGGTTGCCTTAGAG  5400
 H  G  S  A  D  P  A  V  P  K  D          1052
ACATGGCTCCGCTGATCCAGCTGTGGTGCCTAAGGACA  5520
 A  G  A  V  Q  T  A  I  A  C  G  C       1092
AGCCGGTGCCGTCCAAACCGCAATCGCTTGTGGATGCG  5640
 P  Y  F  A  W  L  W  R  Q  G  F  D       1132
GCCATACTTCGCATGGCTGTGGAGGCAAGGGTTTGATG  5760
 D  F  V  I  R  A  G  L  F  W  W  Y       1172
TGACTTCGTCATCAGGGCTGGGTTGTTCTGGTGGTATG  5880
 L  T  E  P  G  L  L  M  L  K  A  L       1212
GTTAACTGAACCCGGTCTCCTAATGCTGAAGGCGCTGT  6000
 L  S  Q  D  G  L  N  Y  A  S  K  R       1252
GTTATCCCAAGACGGGCTCAACTACGCGAGCAAACGGT  6120
 S  M  I  V  Y  E  G  K  F  V  N  P       1292
CTCGATGATTGTTTACGAAGGAAAATTTGTCAACCCAA  6240
 F  H  V  Q  K  L  L  D  S  M  D  E       1332
TTTCCACGTCCAGAAGCTTCTGGATTCAATGGATGAGG  6360
 F  A  Y  M  V  S  W  A  V  Y  L  V       1372
ATTCGCGTATATGGTTTCGTGGGCGGTGTACCTGGTCC  6480
 L  L  G  F  A  G  G  T  V  P  M          1412
GCTGCTGGGTTTCGCAGCAGGTGCACGGTGCCAATGG  6600
 I  S  D  Y  D  Q  E  W  W  G  S  Q       1452
AATTTCTGACTATGACCAAGAATGGTGGGGAGTCAAG  6720
 D  V  E  L  A  Y  T  Q  L  V  Q          1492
CGATGTAGTCGAACTGGCTTACACCCAGCTTGTCCAGG  6840
 I  D  E  T  H  R  V  L  S  Q  F  T       1532
```

```
AATAGACGAGACGCATCGGGTGCTCTCCCAGTTTACTC    6960
 L   M   L   V   R   A   M   R   A   A   K          1572
TCTTATGCTATTAGTACGTGCGATGAGAGCTGCCAAAT    7080
 R   V   K   T   V   W   G   L   T   G   L   V      1612
CAGGGTGAAGACCGTGTGGGGACTCACAGGCCTGGTGG    7200
 D   Y   D   N   F   V   S   N   I   K   E   P      1652
TGATTATGACAACTTTGTCTCCAACATCAAGGAACCCG    7320
 A   A   E   I   C   G   L   K   P   G   E   Y      1692
GGCTGCCGAAATCTGTGGATTGAAGCCTGGGGAGTATG    7440
 D   R   N   P   D   R   I   A   R   S   I   S      1732
AGACAGGAATCCCGACAGGATCGCGCGATCCATAAGCC    7560
 P   E   V   F   A   D   R   D   I   M   L   P      1772
GCCAGAAGTGTTCGCCGATCGAGACATCATGCTCCCTA    7680
 K   Q   A   G   V   M   D   V   I   R   K   N      1812
TAAGCAAGCTGGTGTGTCATGGATGTGATCCGTAAAAACG  7800
 L   L   A   P   R   M   K   D   L   R   T   V      1852
TTTGTTGGCTCCCCGCATGAAGGACTTGCGAACGGTGG    7920
 A   G   S   G   M   P   L   S   Q   S   M   A      1892
TGCCCGGTTCTGGCATGCCTTTGTCACAATCGATGGCTC   8040
 C   K   P   A   L   F   H   G   A   G   K   L      1932
CTGTAAACCAGCATTGTTCCATGGGGCTGGCAAACTGG    8160
 N   A   W   V   M   G   I   T   E   P   S   Y      1972
AAATGCATGGGTCATGGGGATAACCGAACCTTCCTATA    8280
 E   L   L   A   H   N   N   V   N   V   T   E      2012
CGAGCTTCTGGCTCACAATAATGTGAACGTCACTGAGT    8400
 P   A   L   R   L   Q   G   S   S   W   Q   G      2052
TCCAGCATTGCGATTGCAAGGCTCGTCATGGCAAGGTT    8520
 I   K   R   I   V   F   A   N   R   E   V   I      2092
```

```
TATAAAGCGTATTGTCTTCGCCAATCGCGAAGTCATAT  8640
         V  I  S  A  W  A  R  A  T  G  K  P    2132
CGTCATCAGCGCCTGGGCACGCGCTACTGGTAAACCGC  8760
         E  V  D  R  F  K  Q  A  A  A  D  F    2172
CGAGGTTGATCGCTTCAAGCAAGCTGCCGCCGATTTTG  8880
         D  S  A  D  Y  R  A  W  R  Q  G  R    2212
AGATTCAGCGGACTATCGGGCATGGAGGCAGGGAAGGA  9000
         V  Q  N  P  T  A  I  L  M  R  R  T    2252
GGTCCAGAACCCCACGGCTATTCTAATGCGAAGGACTG  9120
         F  Q  P  A  L  Y  K  R  F  A  I  E    2292
ATTCCAGCCCGCACTGTACAAGAGGTTCGCAATTGAGT  9240
         M  Q  V  I  N  V  P  N  W  K  R       2332
GATGCAGGTTATAAACGTGAACCCGAACTGGAAACGGA  9360
         I  H  L  R  I  R  D  D  P  D  P  S  A 2372
CATACACCTCAGGATAAGGGATCCTGACCCCATCCGCG  9480
         Y  T  D  M  I  P  E  E  F  K  R  F    2412
CTACACGGACATGATACCTGAGGAGTTTAAAAGGTTCA  9600
         L  E  T  T  V  D  E  L  T  F  A       2452
GCTGGAAACCACGACCGTTGACGAGTCACGTTCGCCC   9720
         Y  L  K  D  L  L  A  S  E  A  M  I    2492
CTATCTGAAGGATCTCTTGGCCTCCGAGGCCATGATAG  9840
         S  L  F  L  I  G  P  L  Y  N  L  F    2532
GTCACTGTTCTTGATAGGGCCATTATATAATCTATTCA  9960
         I  S  S  I  L  P  R  D  P  Y  M  W    2572
AATCAGCTCGATCCTGCCAAGAGACCCATACATGTGGT 10080
         G  L  A  E  I  I  E  V  L  F  G  R    2612
TGGGTCTCGCCGAGATCATCGAAGTTCTATTTGGGCGCA 10200
         N  P  W  A  A  Y  A  H  T  Y  A  T    2652
```

```
CAATCCTTGGGCCGCGTACGCCCACACGTACGCAACAA  10320
 E   R   N   I   G   I   K   K   L   W   I         2692
GGAGAGGAGGAACATCGGAATCAAGAAACTGTGGATCG  10440
 D   P   S   A   D   I   Y   V   T   T   Y   G     2732
AGACCCATCGGCCGATATCTACGTGACCACGTACGGAC  10560
 L   Q   D   V   E   D   W   K   G   P   T   I     2772
GCTACAGGACGTGGAAGACTGGAAAGGACCAACCATCT  10680
 T   V   Y   K   V   D   S   D   D   V   L   E     2812
TACCGTTTACAAGGTTGATTCCGATGACGTGTTGGAAA  10800
 L   K   K   T   I   A   G   L   E   N   L   D     2852
ACTCAAGAAGACGATTGCTGGATTGGAGAACTTGGACA  10920
 T   G   I   D   I   K   P   A   P   S   I   L     2892
AACTGGCATCGATATCAAACCCGCCCCGTCGATCTTGA  11040
 R   V   N   R   V   G   R   T   M   D   G   V     2932
GAGGGTCAATCGTGTCGGTAGGACGATGGATGGTGTGG  11160
 G   Q   Y   K   V   P   R   L   T   K   V   N     2972
GGGGCAGTACAAGGTCCCCGATTAACTAAAGTCAATG   11280
 Q   S   V   T   K   S   L   F   I   H   L         3012
ACAAAGCGTGACGAAATCGCTCCTGTTTATCCATCTCA  11400
 E   D   H   L   E   R   I   L   T   S   G   K     3052
TGAAGATCATTTGGAGCGCATCTTAACGTCGGGTAAAC  11520
 P   T   I   T   R   P   R   Y   P   C   D   G     3092
CCCCACAATAACGGACCAAGATATCCTTGTGATGGGA   11640
 W   Q   A   Q   V   N   E   L   R   A   Q   N     3132
GTGGCAAGCGCAGGTCAACGAGCTCAGAGCCCAGAACC  11760
 I   P   V   C   G   # #                            3165
TATACCTGTTTGCGGTTAACACAAACCGCCTTCCATTT  11880
TGACATGGTCACTGCCCGTCAGTAAAGACGTTAACCCG  12000
```

FIG.1N

```
GGAGCTGATTCTGTTAACAGCCGCACGGCGAACGGTAGCGTAGATTAAATCTACGGTTTCTGCCTCCTGAGAGATTGGCAGG
CATTCCGGCGAATGGTTAGGCCTCGGAGAGATGCAATTGTGCCTCATCACCACACCGTGACCAATGAGACCAACTCGCAA
GGGCTAGAAATACTAAATACCTTTAACTTGGTGGTAGGCGTGTACCGTGACCCCAGAAGACCCCAGGCTGATGCTT
CTGGAAAAGTAAGCCGGATCCGTCGACGTCTAGAGGATCGTCTACATGTTCAAGAAAATGGGCGAAAAGGGTTGCCCGAAAGTATGG
TTCGGGCGCACTCACAACTGAAATGTTAGTGTTTCAACATCTCAGGAGTTTTAGTGTTACCGTCCTGCGCAAGCAAAGATGAG
AGGCCGCTGCAGTAGGATTCAGACAAATAAATTTTCTCTTGAAAATGTCCGCCGTTTTCTTTTGTTGGCTATTCCCTTTCAC
```

FIG.10

| FIG.1A | FIG.1B |
|---|---|
| FIG.1C | FIG.1D |
| FIG.1E | FIG.1F |
| FIG.1G | FIG.1H |
| FIG.1I | FIG.1J |
| FIG.1K | FIG.1L |
| FIG.1M | FIG.1N |
| FIG.1O | FIG.1P |

FIG.1

```
GGAAACCCGCTGAAGAGTCCAGGACCGAACACGACCAC    12120
AGGAGCAGGAAACACAGTGCAACTGTCGGCCAGCAATA    12240
GTTAGGCAACGGCAATAAGACCGAAGCAAGCACAGAGA    12360
GCTACGCGCTTCGTTGTAAAGCTACCCATACAAAACCC    12480
AACTATACCTTTGACAACAAAGGGTATAGGGATCGGAA    12600
CGTGCGTACGGTGGGAAGAGAACAACAAAG(A)40      12712
```

FIG.1P

GENETICALLY ENGINEERED TRANSMISSIBLE HYPOVIRULENCE

This is a continuation, of application Ser. No. 07/832,117 filed Feb. 6, 1992.

BACKGROUND OF THE INVENTION

Fungi remain a medically, industrially and agriculturally important group of organisms. Opportunistic pathogens such as *Candida albicans* and *Aspergillus fumigatus* can cause serious infections in humans. Recent increases in the incidence of infection of immunocomprised individuals by fungal pathogens has stimulated efforts to develop more effective antifungal therapeutic agents. There is a long history of the use of fungi in the food industry and for the production of biologicals, organic acids and pharmaceutical intermediates. The ability to genetically alter yeast and filamentous fungi by DNA-mediated transformation has considerably increased their industrial potential. Despite impressive progress in the development of chemical fungicides for agricultural application, yield losses due to plant pathogenic fungi remains a significant problem worldwide. The wide spread use of chemical fungicides is also complicated by the persistent development of acquired resistance and by a negative environmental impact.

Few plant disease epidemics have received as much attention or generated as much consternation as the chestnut blight epidemic that occurred in North America and Europe early this century as a result of the unintentional introduction of the Asian fungus, *Cryphonectria (Endothia) parasitica*. Contributing factors include the magnitude of the disease, e.g., an estimated 3.5 billion trees were destroyed in the North American eastern hardwood forest by 1950; the aesthetic, ecological and economic value of the host; and the total inability to devise effect control measures (Anagnostakis, 1982; Roane et al., 1986; Griffin 1986; MacDonald and Fulbright 1991). Consequently reports in the 1960's and 1970's of natural and artificial biological control of chestnut blight due to the phenomenon of "transmissible hypovirulence" generated considerable interest (Grente, 1965; Grente and Berthelay-Sauret, 1978; Van Alfen et al., 1975). Natural variants of *C. parasitica* that exhibited reduced levels of virulence (hypovirulent) were first discovered in Italy and were later identified in different geographic locations in Europe and North America (Grente and Berthelay-Sauret, 1978; Anagnostakis, 1982; MacDonald and Fulbright, 1991). While virulent *C. parasitica* strains penetrate and destroy bark and cambium layers causing wilting and death, hypoviolent strains usually produce superficial cankers that eventually heal as a result of host defense mechanisms. The basis for disease control lies with the ability of the hypovirulence phenotype to be transmitted to virulent strains resulting in conversion of the recipient to hypovirulence (Grente, 1965; Grente and Berthelay-Sauret, 1978; Van Alfen et al., 1975). Studies with auxotrophic mutant strains indicated that the genetic element responsible for the hypovirulence phenotype corresponded to a cytoplasmic determinant that was transferred by hyphal anastomosis (fusion of hyphae) (Van Alfen et al., 1975). Day et al. (1977) subsequently reported that hypovirulent *C. parasitica* strains contained double-stranded (ds) RNA species that were generally absent in virulent *C. parasitica* strains. Moreover, these ds RNAs were observed to be transmitted coincidentally with the hypovirulence phenotype during anastomosis.

Recent characterizations of structural and functional properties of hypovirulence-associated dsRNAs have provided evidence for a viral origin even though these RNAs appear not to have be encapsidated within a discrete virus particle. For example, the large dsRNA, L-dsRNA, present in hypovirulent *C. parasitica* strain EP713 was shown to encode two large polyproteins that undergo autoproteolytic processing during translation (Choi et al., 1991a; 1991b; Shapira et al., 1991a; Shapira and Nuss, 1991). Recent computer-assisted analysis of the predicted amino acid sequences of these polyproteins revealed five distinct domains with significant sequence similarity to previously described conserved domains within protein products encoded by members of the potyvirus group of positive-strand RNA plant viruses (Koonin et al., 1991). Phylogenic trees, derived from the alignment of one specific domain, that of the putative RNA-dependent RNA polymerase, with the sequences of all known viral RNA polymerases strongly suggested that L-dsRNA and potyvirus genomes share a common ancestry. Based on the similarity of the L-dsRNA genetic organization and expression strategy to those of several viral genomes and the apparent evolutionary relationship to the potyviruses, the term hypovirulence-associated virus (HAV) will be used to denote this class of genetic element (Shapira et al., 1991).

Direct analysis of the L-dsRNA present in hypovirulent *C. parasitica* strain EP713 has shown that one strand contains a 3'-poly (A) tail that is base paired to a stretch of poly (U) present at the 5'-terminus of the complementary strand (Hiremath et al., 1986). Sequence analysis of multiple cDNA clones that spanned the entire length of L-dsRNA revealed that the molecule consists of 12,712 bp, excluding the poly(A):poly(U) homopolymer domain, and that only the poly (A) strand contains coding domains of significant size (Shapira et al., 1991). The long open reading frame, designated ORF A, is preceded by a 495 nucleotide (nt) noncoding leader sequence and extends 1,869 nt. The junction between ORF A and ORF B, is contiguous with ORF A and extends 9,498 nt. The junction between ORF A and ORF B consists of the pentanucleotide 5'UAAUG-3' in which the UAA portion serves as a termination codon for ORF A (Choi et al., 1991a) and the AUG portion is the 5'-proximal initiation codon of ORF B (Shapira et al., 1991). An 851 nt 3' noncoding domain follows ORF B, terminating with the 3'-poly (A) tail.

ORF A encodes two polypeptides, p29 and p40, that are released from a polyprotein, p69, by an autocatalytic event mediated by p29 (Choi et al., 1991a). Cleavage occurs between Gly-248 and Gly-249 during translation and is dependent upon the essential residue Cys-162 and His-215 (Choi et al., 1991b). Expression of ORF B also involves an autoproteolytic event in which a 48 kDa polypeptide, designated p48, is released from the N-terminal portion of the encoded polyprotein (Shapira et al., 1991). Cleavage of p48 occurs between Gly-418 and Ala0419 and is dependent upon essential residues Cys-341 and His-388 (Shapira and Nuss, 1991). Both p29 and p48 resemble papain-like proteases. Putative RNA-dependent RNA polymerase and RNA helicase motifs have been located in the C-terminal half of ORF B (Shapira et al., 1991; Koonin et al., 1991).

Efforts to determine the precise genetic information responsible for transmissible hypovirulence have been hampered by the inability of HAV RNAs to initiate an infection by an extracellular route. This is a common property of mycoviruses and unencapsidated viral-like RNAs (Buck, 1986; Wickner 1989; El-Sherbeini and Bostian, 1987). We were recently able to partially overcome this limitation by introducing HAV coding domains into virus-free virulent *C. parasitica* strains by DNA-mediated transformation (Choi and Nuss, EMBO J. 1992). Significantly, transformation with a cDNA copy of the first L-dsRNA open reading frame, ORF A, conferred a number of traits similar to those exhibited by the L-dsRNA-containing hypovirulent strain (EP713). These traits included reduced pigmentation, reduced laccase accumulation and suppressed conidiation, characteristics that frequently, but not universally, accompany hypovirulence-associated traits (listed in Hillman et al. 1990). However, virulence was not reduced in the ORF A transformants. These results established a direct cause and effect relationship between the viral ds RNA present in a hypovirulent c. parasitica strain and specific traits associated with that strain. The fact that these hypovirulence associated traits were conferred in viral-free transformants demonstrated that they are not the result of some general reaction of the fungus to the physical presence of replication viral RNA but are caused by a specific coding domain. The observation that reduced virulence was uncoupled from associated traits such as suppressed sporulation in the ORF A transformants suggests that different viral encoded proteins may be responsible for specific traits expressed by individual hypovirulent strains.

SUMMARY OF THE INVENTION

This invention is a hypovirulent fungus which can transmit the hypovirulence phenotype and avoid vegetative incompatibility. Hypovirulence associated virus is also known as hypovirulence associated genetic element.

A BRIEF DESCRIPTION OF THE FIGURES

The file of this patent contains at least one drawing executed in color.

Figure 1A:
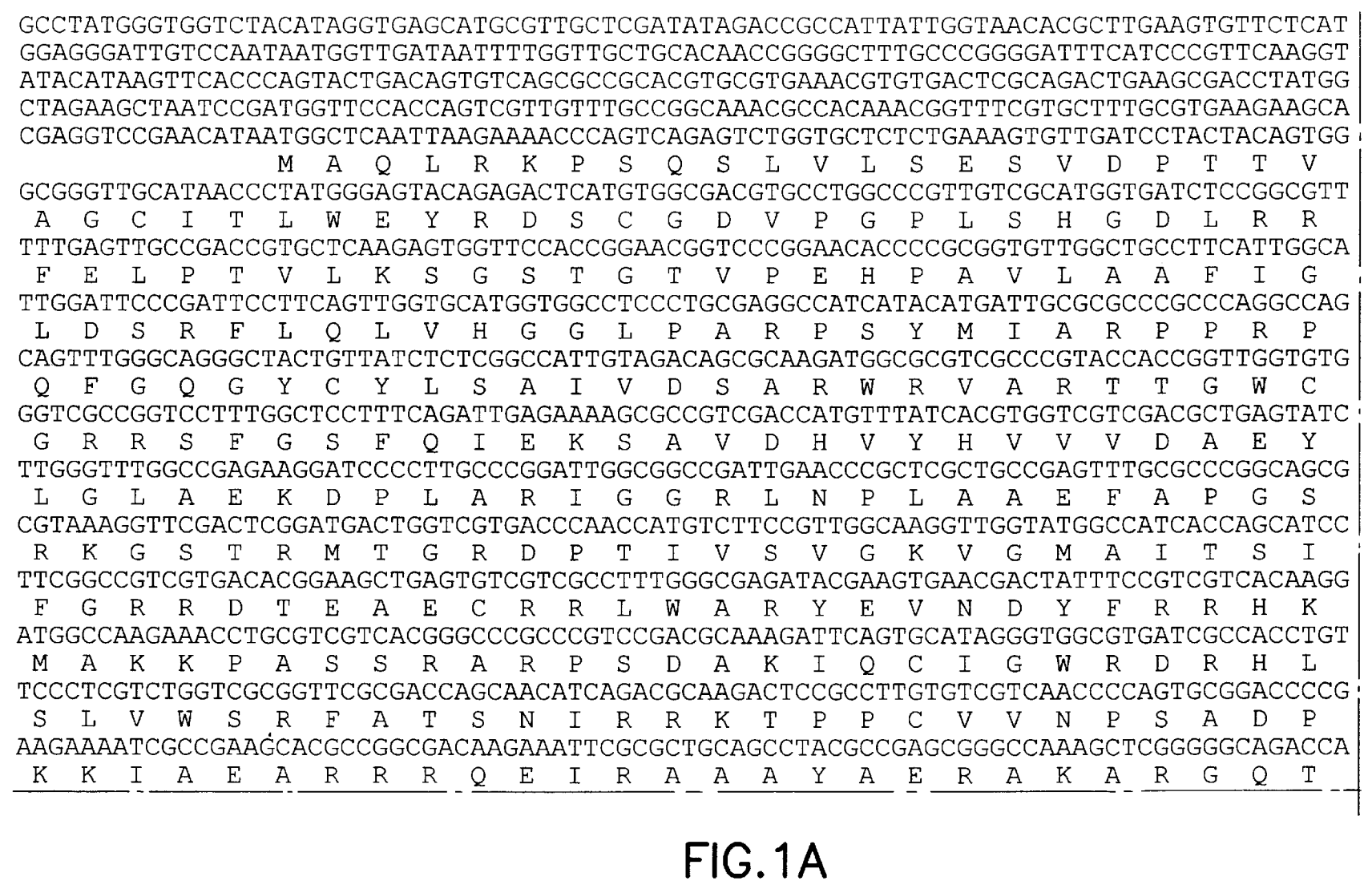
Figure 1G:
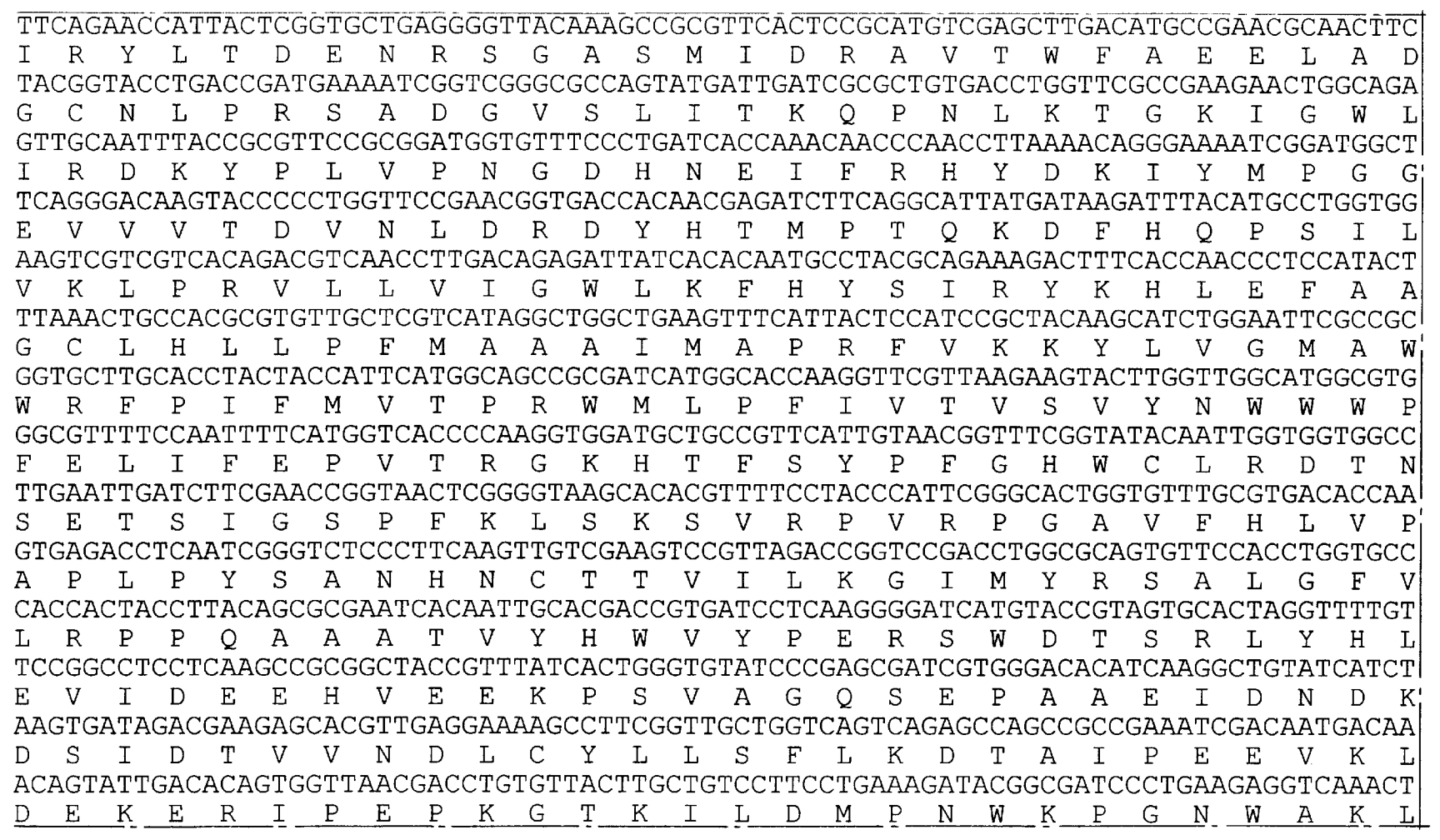
Figure 1K:
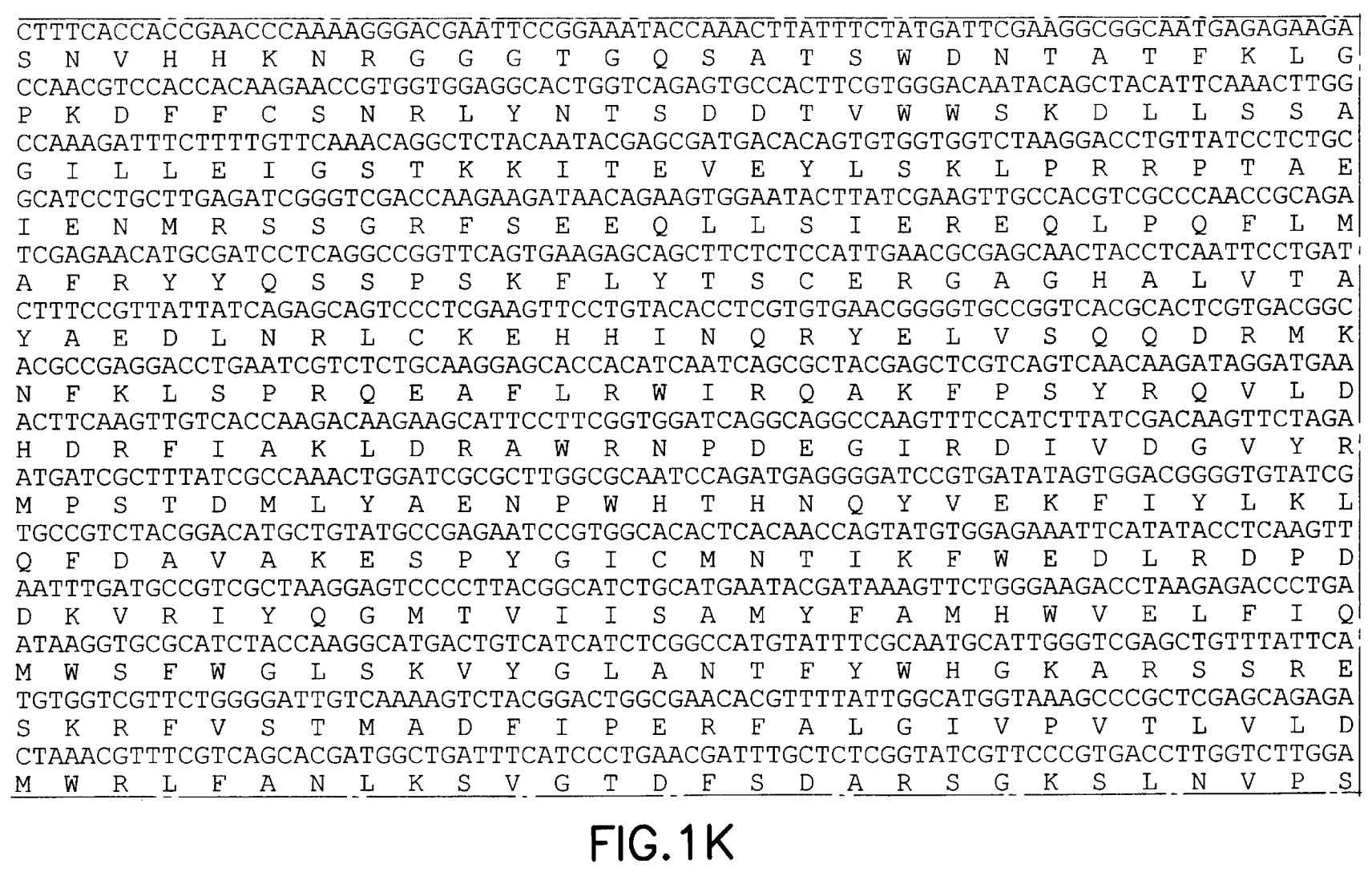
Figure 1M:
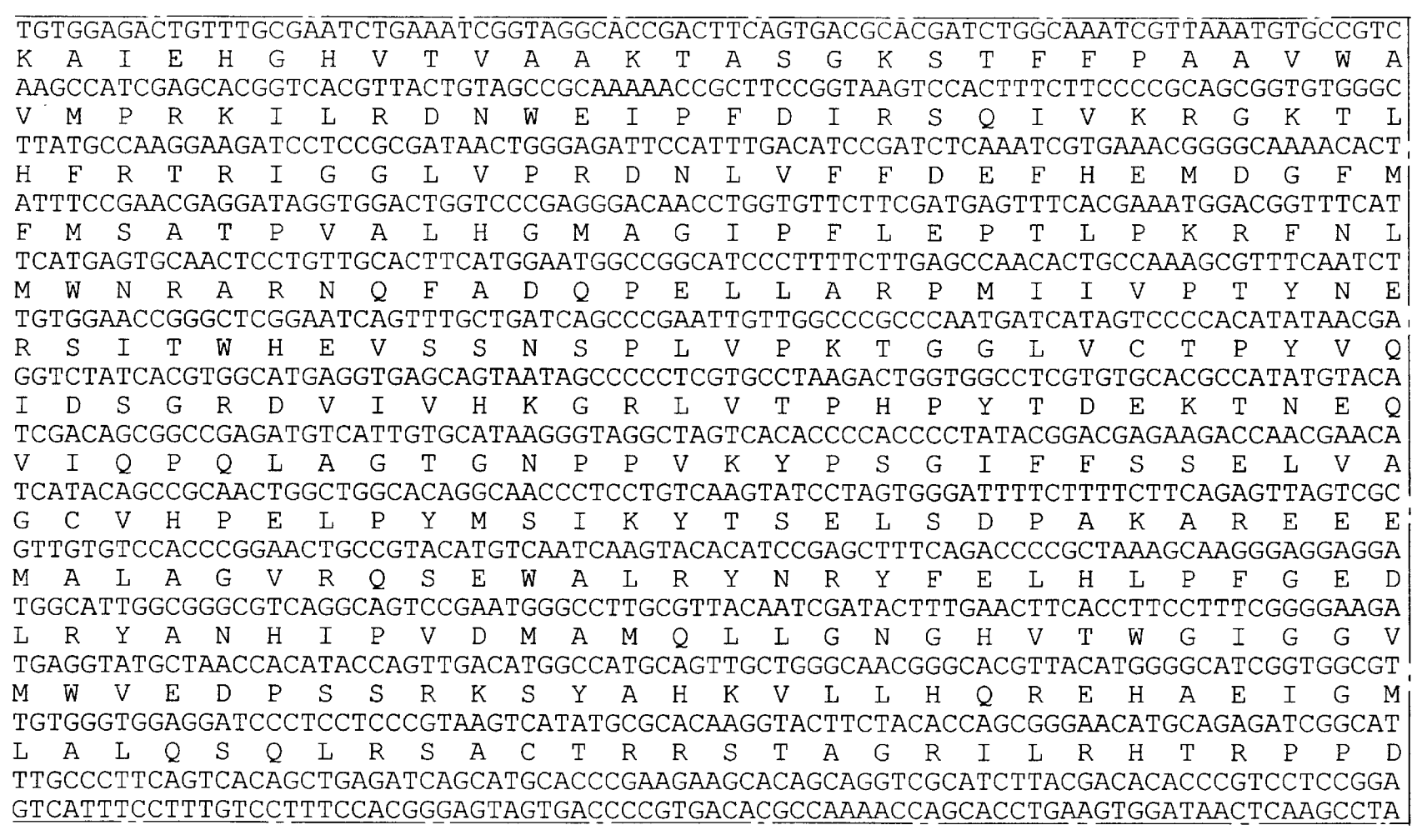

FIG. 1. Complete nucleotide sequence of L-dsRNA present in strain EP713. The sense strand sequence of the cloned cDNA copy of L-dsRNA is shown with number beginning with the 5'-terminal nucleotide. The deduced ORF A (first open reading frame) amino acid sequence is shown below the corresponding nucleotide sequence and extends from the initiation codon at nucleotide position 496–498 to the TAA termination codon, indicated by ###, at nucleotide positions 2362–2364. The ORF B (second open reading frame) amino acid sequence is shown above the corresponding nucleotide sequence and extends from the ATG codon at nucleotide positions 2364–2366 to the TAA codon at nucleotide positions 11859–11861. The GenBank accession number is M57938.

FIGS. 2A and 2B. Description of transformation vectors pAXHY2 and pAXHY5 and Southern analysis of C. parasitica transformants. PanelA. Plasmid pAXHY2 contains the first coding domain of the HAV L-dsRNA, ORFA, flanked by the C. parasitica glyceraldehyde-3-phosphate dehydrogenase gene promoter (Pgpd) and terminator (Tgpd). It was shown that ORFA encodes a polyprotein that is autocatalytically processed into two polypeptides, designated p29 and p40 (Choi et al., 1991a). The gpd-1 promoter region extended 1,696 nt upstream of map position 376 of the published gpd-1 sequence, while the terminator extended from map position 1571 through position 2172 (Choi and Nuss, 1990). This plasmid also contains the E. coli hygromycinB phosphotransferase gene (hygB) proceeded by the Aspergillus nidulans trpC promoter (ptrpC) (Cullen et al., 1987), all in a pUC19 background. Plasmid pAXHY5 is the same as pAXHY2 except that the ORFA coding domain is in the antisense orientation. The location of PstI sites within and flanking the ORFA coding region are also indicated. The arrows located under the ORFA region in each plasmid indicate the sizes of ORFA containing fragments that are expected to be liberated by PstI digestion. PanelB. Shown is the Southern analysis of PstI-digested genomic DNA prepared from four (+)ORFA transformants (A1, A5, A6, A10), two (−)ORFA transformants (a2 and a11), untransformed strain EP155 and hypovirulent strain EP713, all probed with the ORFA coding sequence. The positions of marker fragments are indicated at the left.

FIG. 3. Effect of ORFA transformation on pigmentation and colony morphology. Transformation of EP155 spheroplasts was performed essentially as described (Churchill et al., 1990), followed by selection on hygromycinB-containing medium (40-mg/ml). Transformants used in this study were further selected on a higher level of hygromycinB (200 mg/ml). Transformants containing either vector pAXHY2 [(+)ORFA transformants, A1, A5, A6 or A10] or vector pAXHY5 [(−)ORFA transformants, a2 and a11] were grown in parallel with untransformed EP155 and the isogenic hypovirulent strain EP713 for five days on potato dextrose agar (Difco) on the laboratory bench: light<2,000 lx, temperature 22–24 degrees C. as described (Hillman et al., 1990).

FIG. 4. Effect of ORFA transformation on accumulation of laccase activity. Strains EP155, EP713 and the (+)ORFA and (−)-ORFA transformants were grown for five days in the dark at 22–24 degrees C. on cellophane covering the surface of agar plates containing Bavendamm's medium (Bavendamm, 1928).

FIG. 5. Slot blot analysis of ORF A specific transcripts present in strain EP713 and in ORF A (+) transformants. As indicated in Materials and Methods, each well was loaded with approximately 15 micrograms or denatured ssRNA. The same set of samples were probed first with a DNA fragment that spanned the entire ORF A region (shown at left) and, following stripping of the first probe, with a DNA fragment that corresponded to the coding domain of C. parasitica endothiapepsin gene (epn-1) to provide an indication of the relative amount of cellular mRNA applied to each well. The fungal strains from which the FNA samples were prepared are indicated at the left. Hybridization signals were quantified with the aid of an LKB ULtrascan laser densitometer. THe relative amounts of ORF A specific transcripts present in the fungal strains and transformants were 0%, 100%, 8%, 4%, less than 1%, and less than 1% for EP155, EP713, A1, A5, A6, and A10 respectively.

FIG. 6. Construction of full-length cDNA clone of L-ds RNA (hypovirulence associated virus or genetic element). See Example 2 for details.

FIG. 7. Plasmid $p^{XH9}$.

Table 1. Effect of ORFA transformation on conidiation. Colonies were grown on potato-dextrose agar plates as described in FIG. 2 for 10 days. Conidia were liberated with a glass rod after flooding plates with 10 ml of 0.15% Tween 80. The number of conidia was quantified by direct counting with the aid of a hemacytometer. Results are presented as average number of conidia per ml of the original 10 ml suspension. Strain designations are in FIG. 2. N.D=not determined.

| STRAIN | CONIDIA/ML |
|---|---|
| EP155 | $1.6 \times 10^7$ |
| EP713 | $<1.0 \times 10^4$ |
| a2 | $1.4 \times 10^7$ |
| a11 | $1.7 \times 10^7$ |

-continued

| STRAIN | CONIDIA/ML |
| --- | --- |
| A1 | N.D. |
| A5 | $6.2 \times 10^5$ |
| A6 | $9.5 \times 10^5$ |
| A10 | $3.7 \times 10^5$ |

DETAILED DESCRIPTION OF THE INVENTION

Figure 2A:
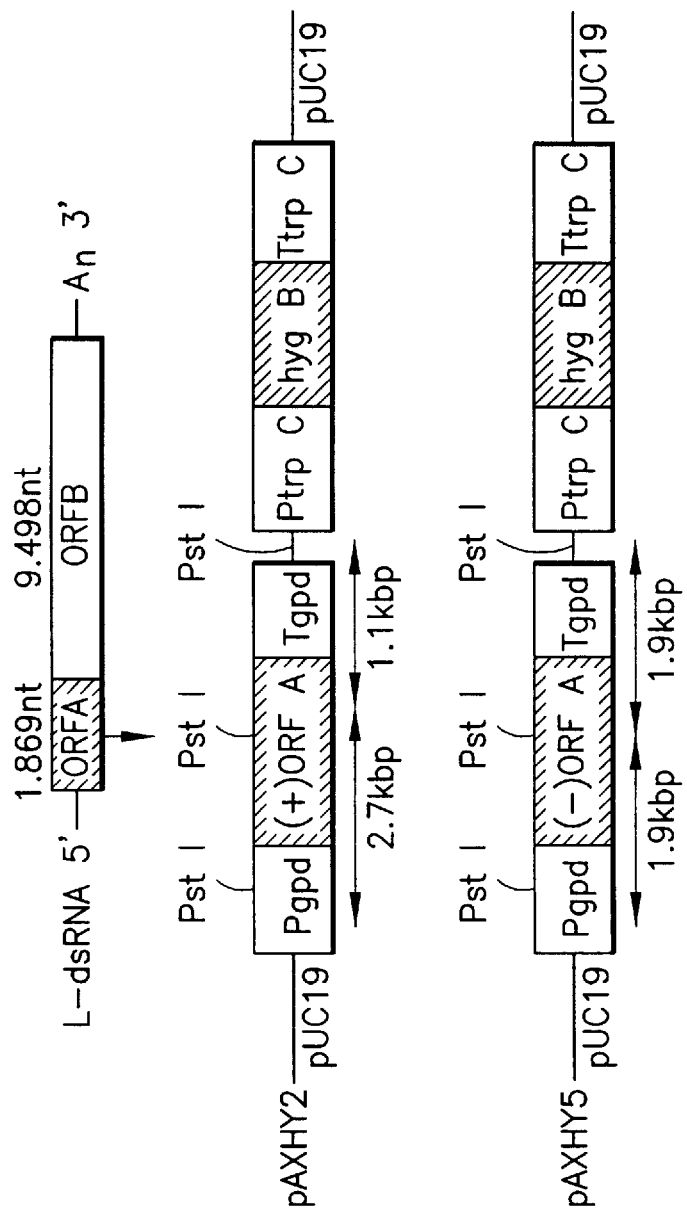

This invention comprises a fungus or fungal spore or parts of either comprising cells of a pathogenic fungus or fungal spore, the nuclear genome of said cells having integrated therein cDNA sequence which is sufficiently homologous to an RNA sequence of a hypovirulence associated genetic element to confer a hypovirulent phenotype which is transmissible. An example is a element or a fungus or fungal spore having a hypovirulent phenotype and the ability to transmit such phenotype by sexual reproduction as a result of a modification to its nuclear genome which modification consists of the integration of a DNA sequence completely or closely homologous to an RNA sequence of a hypovirulence associated virus into said genome resulting in sexually transmissible hypovirulence. Parts of the fungus include mycelia and hyphae.

The fungus or fungal spore may be a plant or an animal pathogen. Examples of plant pathogens are *Cryphonectria parasitica, Ophiostoma ulmi, Gaeumannomyces graminis, Helminthosporium victoriae, Ustilago maydis, Phytophthora infestans,* or *Rhizoctonia solani.* These pathogens are are described in Nuss and Koltin, Ann. Rev. Phytopanthol. 1990, 28:37–58, and possess dsRNAs (i.e. genetic elements).

A preferred RNA sequence is the RNA sequence of a hypovirulence associated genetic element of *C. parasitica.* An example is strain EP 713. Such RNA is isolated as described in Hillman et al., 1990, however any conventional means is acceptable.

The invention in particular includes a fungus or fungal spore or parts of either comprising cells of a pathogenic fungus or fungal spore, the nuclear genome of said cells having integrated therein a cDNA sequence which is sufficiently homologous to the second open reading frame of the RNA sequence of a hypovirulence associated genetic element of *C. parasitica* to confer a hypovirulent phenotype which is transmissible without repressing sporulation capacity. Strain EP 713 is an example.

The integrated DNA may have the sequence shown in FIG. 1. cDNA is produced by conventional means (see Maniatis et al). Specifically, obtaining cDNA from RNA is described in Shapiro et al (1991). Any conventional means is contemplated.

Also, part of this invention are three cDNA polynucleotides sequences. Sequences are provided in FIG. 1. The whole EP 713 genetic element is the sequence of FIG. 1. The first open reading frame (ORF A) is from about nucleotide 496–98 to about 2362–64 of FIG. 1, and the second (ORF B) from about 2364-to about 11859–61 of FIG. 1.

A vector suitable for expression in fungi which contains any one of these three polynucleotide sequences is part of this invention.

Suitable vectors may contain a fungal promoter and a fungal terminator, and optionally a marker suitable for expression in fungi. Conventional vectors may be used. Methods for producing vectors using recombinant DNA technology are well known in the art.

In particular, a vector may contain the *C. parasitica* glyceraldehyde-3-phosphate dehydrogenase gene promoter and terminator. Specific vectors are pAXHY2, pAXHY5 and pXY9, described in Example 1 and 2.

Also included in this invention is an isolated polypeptide having the amino acid sequence of FIG. 1, an isolated polypeptide having the amino acid sequence from about amino acid 1 to about amino acid 622 of FIG. 1 (ORF A) and an isolated polypeptide having the amino acid sequence from about amino acid 1 to about amino acid 3165 of FIG. 1 (OFR B). Antibodies to these polypeptides are included. Antibodies and polypeptides can be produced and isolated by conventional methods. Polypeptides can be isolated by known means from fungi, or produced by known methods recombinantly using the DNA sequence of FIG. 1. For specific examples of antibody production, see Rae et al. 1989.

This invention also includes a method for producing a fungus or fungal spore or parts of either comprising cells of a pathogenic fungus or fungal spore having a hypovirulent phenotype which is transmissible which comprises integrating a cDNA sequence sufficiently homologous to an RNA sequence of a hypovirulence associated genetic element into the genome of said fungus or fungal spore or parts so as to confer sexually or vegetatively transmissible hypovirulence on the fungus or fungal spore.

Another aspect of the invention is a method for producing a protein in a fungus which comprises inserting into a fungus a vector comprising a DNA sequence homologous to the second open reading frame of the RNA sequence of a hypovirulence associated gentic element of *C. parasitica* strain EP713 and a DNA sequence encoding the protein; and culturing the fungus to cause multiple copies of the vector to generate and express, thereby causing production of the protein. This is an example of a high copy number cytoplasmic expression vector.

A method for treating fungal diseases which comprises administering to an organism infected with a virulent fungus a composition containing a fungus or fungal spore or parts of either comprising cells of the virulent fungus or fungal spore, the nuclear genome of said cells having integrated therein a cDNA sequence which is sufficiently homologous to an RNA sequence of a hypovirulence associated genetic element to confer a transmissible hypovirulent phenotype and a suitable carrier, said fungus or fungal spore or parts being present in amounts sufficient to retard the growth of virulent fungus by converting the preponderance of infecting fungi to a hypovirulent phenotype is part of this invention. The organism may be a plant.

In particular, a method for treating chestnut blight which comprises administering to plants infected with *C. parasitica* a composition containing a fungus or fungal spore or parts of either comprising cells of *C. parasitica,* the nuclear genome of said cells having integrated therein a cDNA sequence which is sufficiently homologous to the RNA sequence of a hypovirulence associated genetic element of *C. parasitica* to confer a transmissible hypovirulent phenotype and a suitable carrier, said fungus or fungal spore or parts being present in amounts sufficient to retard the growth of convert the preponderance of infecting fungi to a hypovirulent phenotype is included. The composition may be delivered as a spray, and may contain a paste made up of the mycelia or hyphae of the fungus. (See Anagnostakis 1984 and Grente and Berthelay-Sauret 1978).

Also included is a composition which comprises a fungus or fungal spore or parts of either comprising cells of the virulent fungus or fungal spore, the nuclear genome of said cells having integrated therein a cDNA sequence which is sufficiently homologous to an RNA sequence of a hypovirulence associated genetic element to confer a transmissible hypovirulent phenotype, and a suitable carrier.

For example, the composition may be in the form of a liquid, or powder. The RNA sequence may be that of a hypovirulence associated virus or genetic element of C. parasitica strain EP713.

For example, the composition may include a cDNA sequence which is completely or closely homologous to the second open reading frame of the RNA sequence of a hypovirulence associated virus of C. parasitica strain EP713.

Various formulations of the compositions are possible and are produced by conventional methods. Agronomically acceptable adjuvants and carriers are employable to disperse the fungi, spores, or active portions thereof. Precise formulations and dosages may be selected to best facilitate the spread of hypovirulence for a given application.

The composition may be aqueous, a dust or powder, a wettable powder, an emulsion, a granular form a paste or any known type of formulation depending on how it is to be applied. As examples of means of application, a paste, in particular paste made up of fungal mycelia or hyphae with appropriate carriers and components as described below, could be applied directly to plants. Powders can be dispersed by air, and aqueous solutions sprayed. Another application method is to bore holes around the periphery of a canker of an infected plant, and insert into the holes mycelial paste as described above.

The fungus or spore cell concentration should be at a level which provides for establishment of the fungus or spore cells on the treated plants and for their ability to multiply and transmit their hypovirulent phenotype to infecting virulent fungi.

Compositions may include additives such as surfactants, nutrients, buffers, biological or chemical pesticides, and pentrating agents, in particular in the case of aqueous compositions. Included in particular in dry compositions are inert powders, stablizing agents, salts, anticaking agents, nutrients, buffers, film-forming material.

Aqueous compositions may be aerosels, foliage sprays, mists, and other known compositions.

A method for treating chestnut blight which comprises administering to plants infected with C. parasitica a composition containing a fungus or fungal spore or parts of either comprising cells of C. parasitica, the nuclear genome of said cells having integrated therein a cDNA sequence which is sufficiently homologous to the RNA sequence of the second open reading frame of the RNA sequence of a hypovirulence associated genetic element of C. parasitica to confer a hypovirulent phenotype which is transmissible without repressing sporulation capacity and a suitable carrier, said fungus or fungal spore or parts being present in amounts sufficient to retard the growth of infecting fungi by converting the preponderance of infecting fungi to a hypovirulent phenotype without affecting sporulation is also part of this invention.

EXAMPLE 1

Figure 2B:
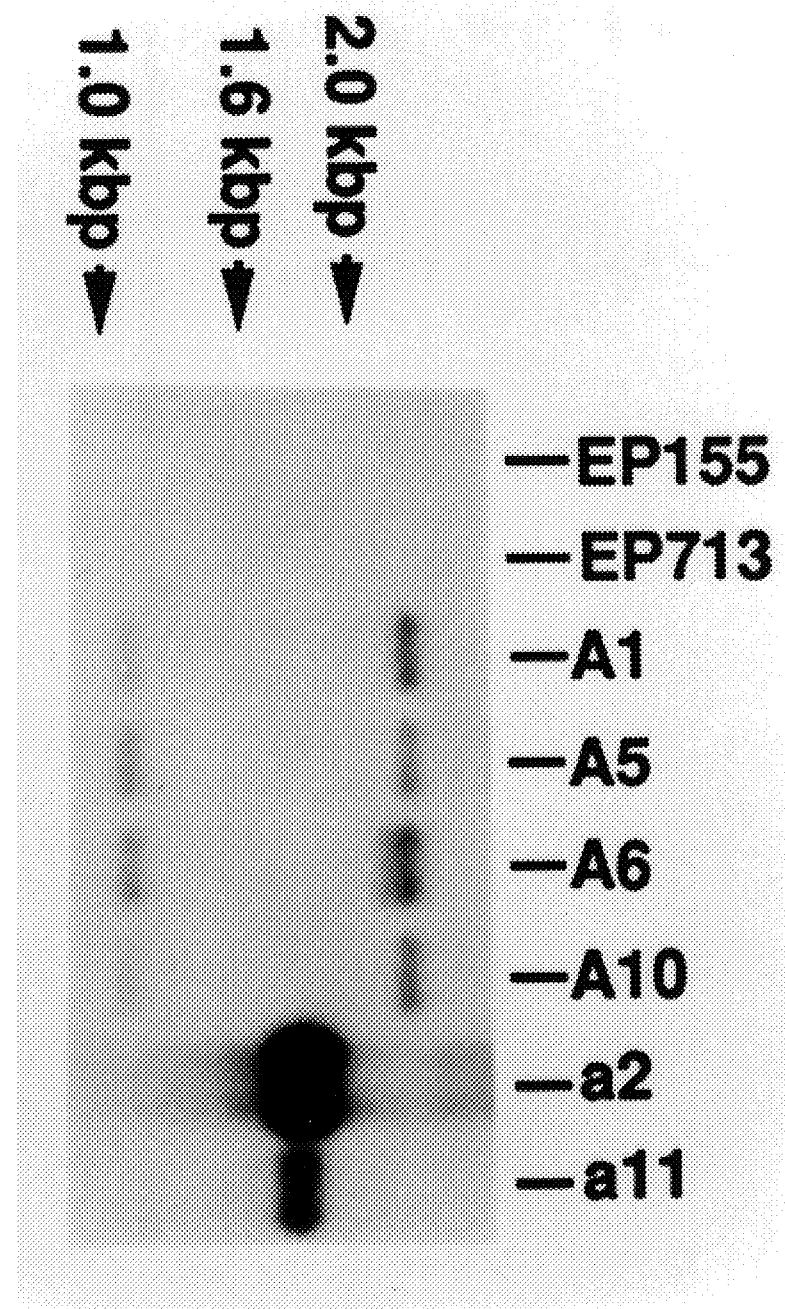

The potential phenotypic contribution of the first open reading frame present in L-dsRNA, ORFA, was tested by transforming virulent C. parasitica strain EP155, which is isogenic to the L-dsRNA-containing hypovirulent strain EP713, with vector pAXHY2. This vector contains the ORFA coding domain fused upstream to the C. parasitica glyceraldehyde-3-phosphate dehydrogenase (gpd-1) promoter and fused downstream to the gpd-1 terminator (FIG. 2A). pAXHY2 also contains the Escherichia coli hygromycinB phosphotransferase gene as a selectable marker flanked by the trpC promoter and terminator domains from Aspergillus nidulans (Cullen et al., 1987). Plasmid pAXHY5, which contained ORFA in the reverse orientation, served as a control vector. Selected transformants were subjected to Southern hybridization analysis to confirm integration of the appropriate transformation vector. Two different sets of ORFA-containing fragments are liberated from each vector by PstI digestion, fragments of 2.7 kb and 1.1 kb from pAXHY2 and two 1.9 kb fragments from pAXHY5 (illustrated in FIG. 2A). As shown in FIG. 2B, fragments of the expected size were observed when a blot containing PstI-digested genomic DNA of four independent pAXHY2 transformants [designated (+)ORFA transformants A1, A5, A6 and A10] and two independent pAXHY5 transformants [designated (-)ORFA transformants a2 and a11] was probed with the ORFA sequence. Based on the relative intensity of the hybridized bands, it appeared that each of the four (+)ORFA transformants contained the same approximate number of copies of integrated pAXHY2 DNA, while the copy numbers for the two (-)ORFA transformants were several fold higher. No homology to ORFA sequences was observed for genomic DNA prepared from either strain EP155 or EP713.

The isogenic virulent and hypovirulent strains EP155 and EP713 exhibit clearly observable phenotypic differences that provide convenient markers for transformation studies aimed at examining the consequence of introducing HAV genetic information. When grown under standard laboratory conditions, strain EP155 is orange in color, conidiates abundantly and produces consistent levels of phenol oxidase activity of the laccase type. In contrast, strain EP713 appears white, is severely suppressed in conidiation and produces significantly reduced levels of laccase (Hillman et al., 1 990).

Figure 3:
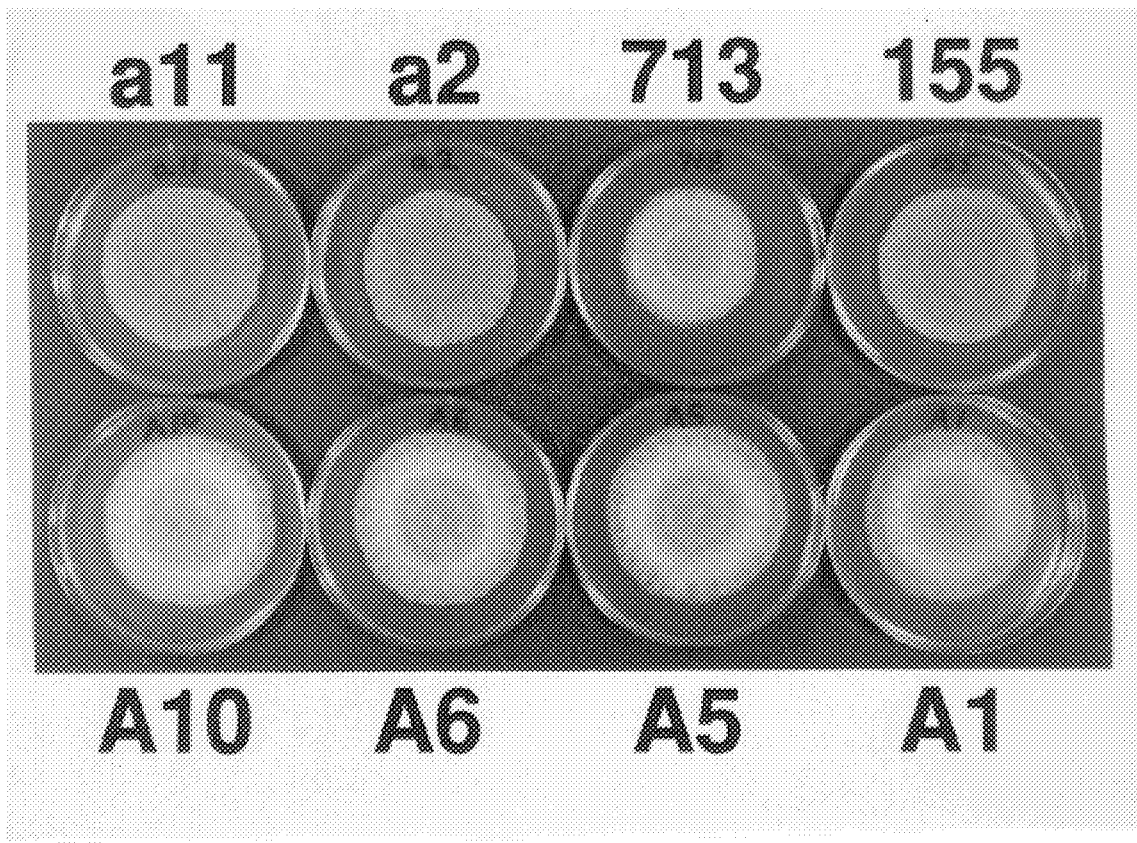

As indicated in FIG. 3, transformation with the (-)ORFA vector pAXHY5 resulted in no alteration in colony morphology or reduction in pigmentation (compare transformants a2 and a11 with EP155). This result indicates that the introduction of vector sequences, including the hygromycinB phosphotransferase gene, does not significantly alter fungal phenotype. Remarkably, the four independent (+)ORFA transformants, A1, A5, A6 and A10, all resembled strain EP713. Pigment production was severely reduced throughout the culture period in which the colonies were actively expanding. However, unlike the situation with strain EP713, mature (+)ORFA transformant colonies did develop a very low level of pigmentation. It is noteworthy that no alterations in pigmentation were previously observed among any hygromycin resistant isolates generated from numerous unrelated transformation experiments. In contrast, all (+) ORFA transformants, including the four presented here, showed reduced pigment production.

Figure 4:
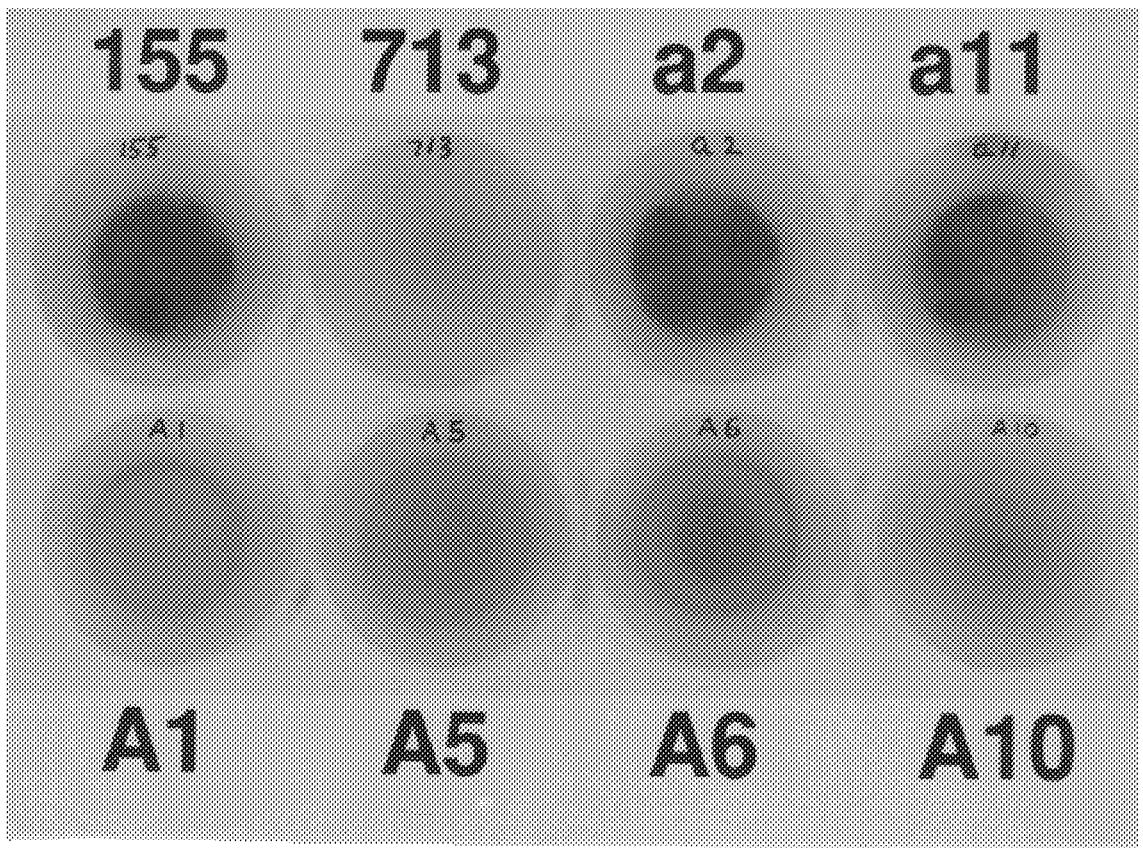
Figure 5:
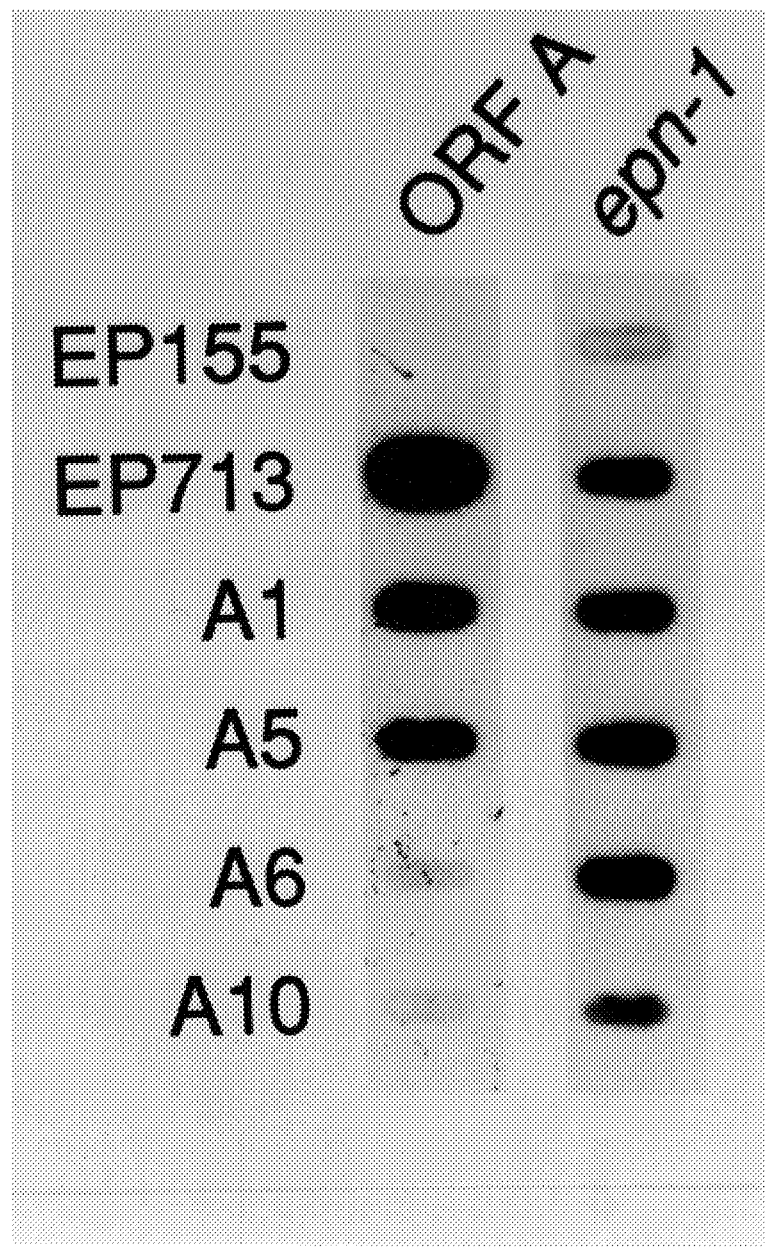

There have been several reports that hypovirulent C. parasitica strains are deficient in phenol oxidase activity of the laccase type (Hillman et al., 1990; Rigling et al., 1989) and that the difference in relative laccase levels can readily be detected by a color reaction on Bavendamm's medium (Rigling et al., 1989). As indicated in FIG. 4, strain EP155 when grown on this medium produces a dark brown color, while strain EP713 exhibits a very weak color reaction. Similar to the results observed for pigmentation, transformants a2 and a11 resembled EP155 in terms of color reaction while laccase accumulation was reduced in all four (+)ORFA transformants. However, there was some apparent variation in the level of laccase reduction. Transformant A6 exhibited a slightly darker color reaction than did transformant A10, and laccase activity appeared to be reduced less in all four (+)ORFA transformants than in strain EP713.

Suppressed conidiation is another common hypovirulence-associated characteristic. The level of suppression in the case of strain EP713 is consistent and nearly complete under standard laboratory conditions (Hillman et al., 1990, Table 1). As indicated in Table 1, the (-)ORFA transformants produced conidia at a level comparable to that of the untransformed EP155 control. In contrast, (+)ORFA transformants produced conidia at a level between 16 and 40fold less than the level produced by the EP155 control. However, the level of suppression, while significant, was much less than that of the EP713 control (Table 1).

The observation that (+)ORFA transformants exhibited a number of hypovirulence-associated traits prompted us to examine whether virulence was also reduced in these transformants. Dormant chestnut stems were inoculated (Jaynes and Elliston, 1980) and the relative virulence, as a function of the mean canker radial growth, was analyzed (SAS system for personal computer release 6.04 from SAS Institute Inc., Cary, N.C.). There was no significant difference between the canker sizes for (+)ORFA (A6 and A10) and (-)ORFA (a2 and a11) transformants and all four transformants produced cankers at least 5 times larger than the EP713 cankers (data not shown). Based on this assay, there was no evidence that the (+)ORFA transformants were reduced in virulence.

The uncoupling of hypovirulence from associated traits is highly significant and shows that hypovirulent strains could be engineered to exhibit specific traits. It is possible to delete portions of the HAV sequence that are, for example responsible for reduced levels of sporulation while modifying other portions of the molecule to enhance hypovirulence. Introduction of these engineered molecules into virulent fungal strains by various means can result in the generation of hypovirulent strains which disseminate through abundant sporulation. A specific L-dsRNA coding domain, in the absence of replicating HAV RNA, is sufficient to confer certain traits that are exhibited by the corresponding untransformed hypovirulent strain. This result established a direct cause and effect relationship between the viral dsRNA present in a hypovirulent C. parasitica strain and specific traits associated with that strain. Additionally, it clearly demonstrates that these phenotypic traits are not the result of some general reaction of the fungus to the physical presence of replicating viral RNA but are caused by specific viral coding domains.

MATERIALS AND METHODS

Fungal strains and growth conditions. C. parasitica strains EP155 (virulent, dsRNA-free) and EP713 (isogenic to EP155, hypovirulent, contains L-dsRNA) were maintained as described previously (Hillman et al., 1990). Transformed strains were grown on potato dextrose agar (Difco) on the laboratory bench: light<2,000lx, temperature 22–24 degrees C. as described by Hillman et al., (1990). To test for laccase activity, colonies were grown in the dark at 22–24 degrees C. on cellophane covering the surface of agar plates containing Bavendamm's medium (Bavendamm, 1928).

Transformations. Transformation vector pAXHY2 contained the entire first open reading frame, ORFA, of L-dsRNA flanked by the C. parasitica glyceraldehyde-3-phosphate dehydrogenase gene (gpd-1) promoter and terminator and the E. coli hygromycinB phosphotransferase gene proceeded by the Aspergillus nidulans trpC promoter (Cullen et al., 1987) all in a pUC19 background (see FIG. 2A). The gpd-1 promoter region extended 1,696 nt upstream of map position 376 of the published gpd-1 sequence, while the terminator extended from map position 1571 through position 2172 (Choi and Nuss, 1990). Transformation of EP155 spheroplasts was performed essentially as described by Churchill et al. (1990), followed by selection on hygromycinB- containing medium (40 mg/ml).

EXAMPLE 2

Figure 6:
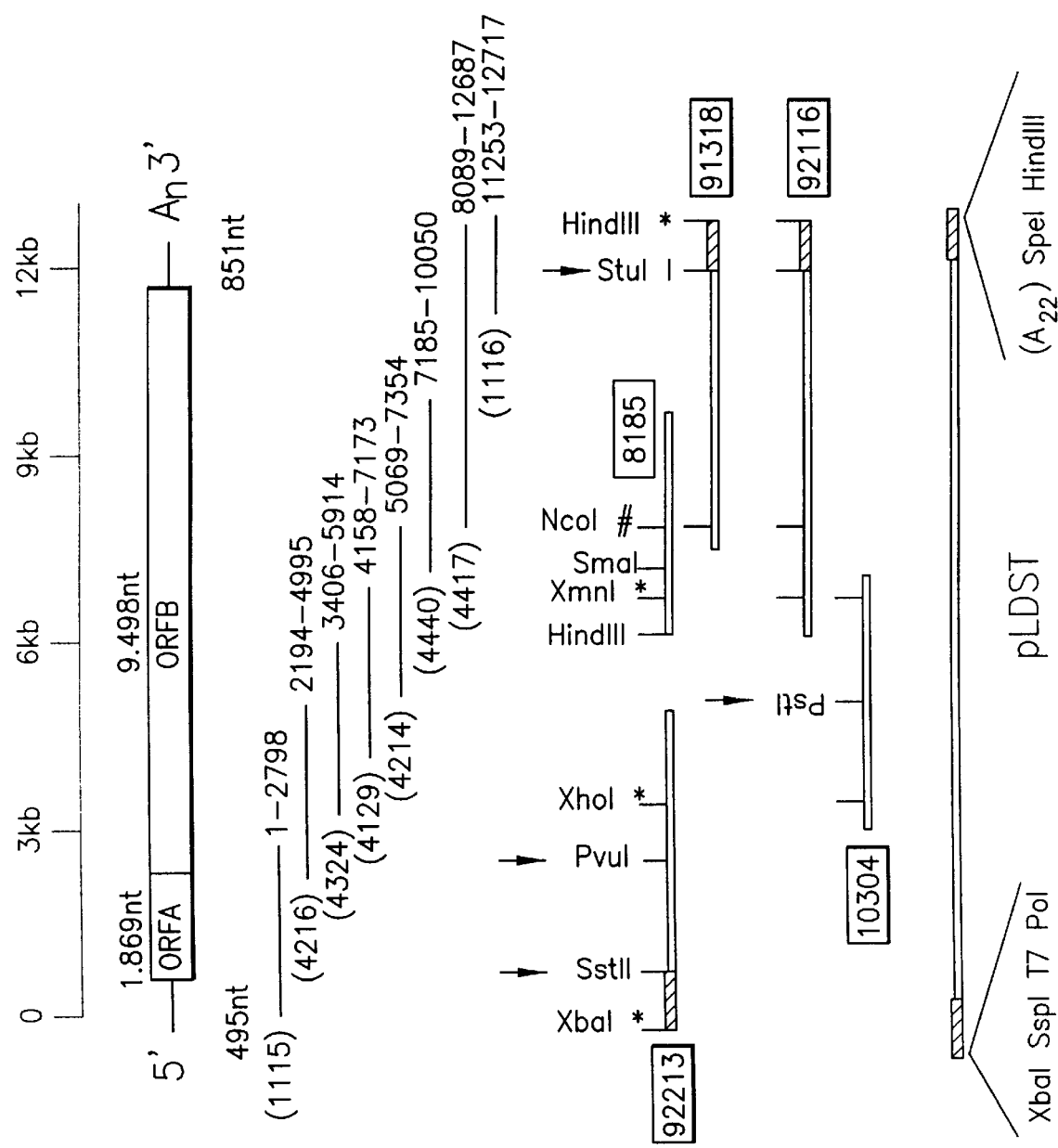
Figure 7:
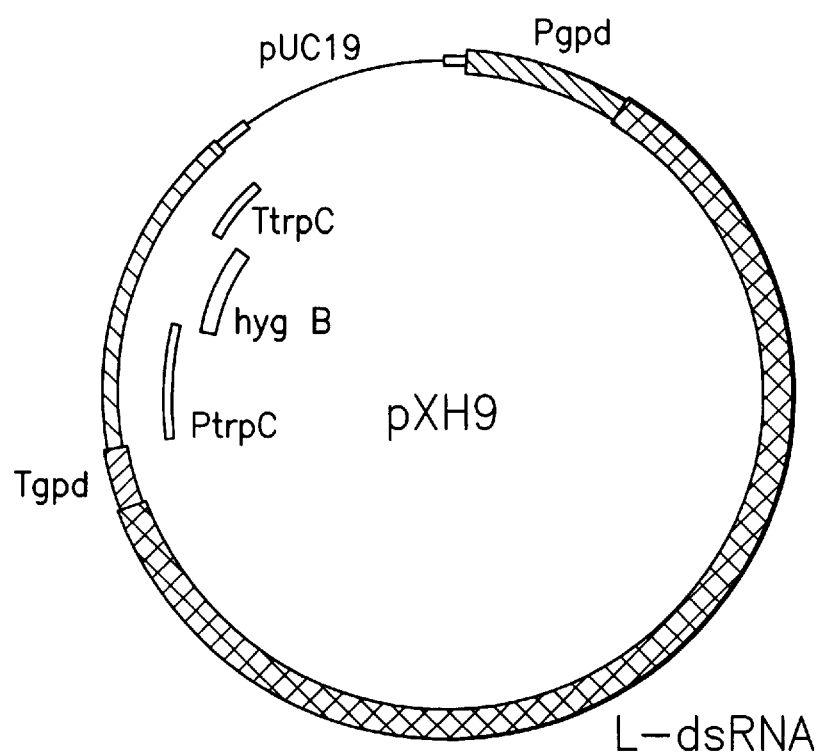

The manipulations used to construct a full-length cDNA clone of L-dsRNA are indicated in FIG. 6. Several large intermediate clones were first generated from the set of partial cDNA clones initially used to derive the L-dsRNA nucleotide sequence and genetic map. Additionally, modifications were introduced into the terminal regions of the L-dsRNA sequence with the aid of the polymerase chain reaction (PCR)(Saiki et al., 1988). These included the addition of XbaI and SspI sites at the end corresponding to the 5'terminus of the coding strand as subsequent cloning aids. A sequence corresponding to the bacteriophage T7 polymerase promoter was also fused to the L-dsRNA sequence. Modifications introduced into the other terminus included a 22 residue long stretch of poly (A): poly (U) to stimulate the natural heteropolymer domain followed by SpeI and HindIII sites. A four factor ligation-transformation was then performed to generate a plasmid, pLDST, that contained the full-length L-dsRNA clone in a pUC19 background. The unique SspI and SpeI sites introduced at the termini of the L-dsRNA sequence by PCR facilitate subsequent subcloning of the intact L-dsRNA cDNA compliment into suitable C. parasitica transformation vectors. For the purposes of this study, the SspI/SpeI fragment was subcloned into transformation vector pCPXHY1 to yield plasmid pXH9 (FIG. 7). This construct contains the entire L-dsRNA sequence with the PCR-modified termini fused upstream to the C. parasitica glyceraldehyde-3-phosphate dehydrogenase (gpd-1) promoter and fused downstream to the gpd-1 terminator. pXH9 also contains the Escherichia coli hygromycin B phosphotransferase gene as a selectable marker flanked by the Aspergillus nidulans trpC promoter and terminator domains (Cullen et al., 1987), all in a pUC19 genetic background.

L-dsRNA cDNA is Infectious

Hypovirulent C. parasitica strains often exhibit traits in addition to reduced virulence that distinguish them from virulent strains. These so-called hypovirulence-associated traits vary among individual hypovirulent strains but commonly include suppressed sporulation, reduced pigmentation and reduced accumulation of specific enzymatic activities or metabolites. Therefore, differences are exhibited between the L-dsRNA-containing hypovirulent strain EP713 and its virus-free isogenic virulent strain EP155 in transformation studies. Under standard laboratory conditions, strain EP155 produces orange pigments, conidiates abundantly, and produces easily measurable levels of phenol oxidase activity of the laccase type. In contrast, strain EP713 is white in appearance, is suppressed in conidiation and produces significantly reduced levels of laccase (Hillman et al., 1990). Using a transformation vector similar to pXH9, we observed that introduction of the L-dsRNA ORF a coding domain into strain EP155 conferred most of the hypovirulence-associated traits characteristic of strain EP 713 but failed to confer hypovirulence (Choi and Nuss, 1992).

The observation that ORF-A alone could confer hypovirulence-associated traits suggest that these same traits could be used to initially score pXH9 transformants. In fact, most of the hygromycin resistant pXH9 transformants did exhibit EP713-like traits as exemplified by transformants CN2, CN3, CN6 and CN7. These transformants failed to produce orange pigments or to produce any asexual spores under standard laboratory conditions and appeared to be slightly retarded in the rate of growth in comparison to both strain EP 155 and EP713. The EP713-like pXH9 transformants also gave a very weak color reaction when grown on Bavendams medium indicating a deficiency in laccase accumulation as has been reported for strain EP713 (Hillman et al., 1990) and other natural hypovirulent strains (Rigling et al., 1989). It is noteworthy that the hypovirulence-associated traits exhibited by these pXH9 transformants were significantly more severe than was observed for the ORF A transformants. For example, sporulation was reduced between 16 and 40 fold in the ORF A transformants but was completely suppressed in the pXH9 transformants. Hygromycin resistant colonies that exhibited EP155-like traits were also observed among the pXH9 transformants at a rate of approximately 10%, as exemplified by transformants CN4 and CN5.

Since transformants that contained an integrated form of ORF A exhibited hypovirulence-associated traits in the absence of viral replication, the ability of pXH9 to confer similar traits might also be the result of exclusive expression from integrated copies of the L-dsRNA cDNA. Alternatively, since pXH9 contains the entire L-dsRNA sequence, including the putative RNA-dependent RNA polymerase and RNA helicase coding domains, the possibility existed that the L-dsRNA sequence could be resurrected from the cDNA copy as a cytoplasmically replicating dsRNA form as has been reported previously for cDNA copies of Poliovirus and bacteriophage Qβ genomes (Taniguchi et al., 1978; Racaniello and Baltimore, 1981). The four EP713-like pXH9 transformants was found to harbor a dsRNA species that comigrated with L-dsRNA extracted from strain EP713. In contrast, the two EP155-like pXH9 transformants lacked any detectable dsRNA species. Strain EP713 contains other dsRNA species in addition to L-dsRNA that have been shown to represent internally deleted forms of L-dsRNA (Shapira et al., 1991b). One particularly abundant family of defective dsRNA, the M-dsRNAs (8 to 10 kbp) has been consistently found in every dsRNA fraction prepared from strain EP713 and has been observed to invariably co-segregate with the L-dsRNA species in a single conidial isolates. The absence of the M-dsRNA species in the pXH9 transformants is consistent with the finding that the L-dsRNA species was recently resurrected from an integrated copy of L-dsRNA cDNA.

Transmissibility of Conferred Traits

A hallmark of transmissible hypovirulence is the ability of the hypovirulence phenotype to be transmitted to vegetatively compatible virulent strains by hyphal anastomosis coincident with the transfer of hypovirulence-associated viral RNAs (Van Alfen et al., 1975). Consequently, a functional test of the biological activity of the putative resurrected L-dsRNA species would be to examine whether the traits exhibited by the pXH9 transformants could be cytoplasmically transmitted via hyphal anastomosis. Anastomosis-mediated conversion of a virulent strain to the hypovirulence phenotype can be monitored visually in the laboratory by the paired inoculation on an agar plate of a normally orange virulent strain and a vegetable compatible white hypovirulent strain. Inoculation points are positioned so that the two colonies intersect within the first two days of culture. The converted virulent hyphae appear as a wedge of white mycelium that initiates at the interface between the colonies and extends along the periphery of the virulent colony. In fact, this pattern was observed when virulent strain EP155 was paired with pXH9 transformant CN2 indicating that the resurrected L-dsRNA is transmissible via anastomosis.

To confirm the apparent conversion of virulent strain EP155 by the resurrected L-dsRNA, mycelial samples from various portions of the paired colonies were characterized with respect to hygromycin B resistance, colony morphology and presence of L-dsRNA. As expected, samples taken from the CN2 colony carried the hygromycin B phosphotransferase marker, produced white colonies and contained L-dsRNA. In contrast, samples taken from the orange portion of the EP155 colony failed to grow in the presence of hygromycin B, produced orange colonies and lacked any dsRNAs. Significantly, samples taken from the converted periphery of the EP155 colony also failed to grow in the presence of hygromycin B, but produced white colonies and were found to contain dsRNAs. Interestingly, the dsRNA fraction extracted from the latter samples contained species in addition to L-dsRNA that were not found in the original CN2 transformant. Although these new dsRNAs were similar in size to the M-dsRNA species present in strain EP713, they were shown not to co-migrate with the M-dsRNAs when subjected to further electrophoresis.

The relationship between anastomosis and the generation of internally deleted defective forms of L-dsRNA is currently unclear due to the limited sample size analyzed to date. However, given the impact that defective RNAs have on symptom expression in other viral systems (Roux et al., 1991), this subject warrants further investigation.

The Infectious L-dsRNA cDNA Clone Confers the Complete Hypovirulence Phenotype Dormant chestnut stems were inoculated (Jaynes & Elliston 1980) and relative virulence as a function of mean canker radial growth was analyzed. Converted strains which contained the resurrected ds L-RNA (or genetic element) and integrated cDNA copy or that contained the resurrected as RNA but lacked the integrated cDNA copy had the same reduced virulence (hypovirulence) as the corresponding natural hypovirulence strain.

Transformation of an isogenic, virus-free, virulent C. parasitica strain with the full-length L-dsRNA cDNA clone resulted in transformants that expressed the complete hypovirulence phenotype and that contained a resurrected cytoplasmically replicating form of L-dsRNA that was transmissible via hyphal anastomosis.

The availability of an infectious cDNA clone of an HAV dsRNA makes it possible to employ site-directed and specific deletional mutagenesis to generate a collection of defined L-dsRNA mutants that contain defects in any desired portion of the molecule. L-dsRNA modulates the expression of specific fungal genes by selectively altering regulatory pathways (Choi et al., 1992); Rigling and Van Alfen 1991). A collection of mutant L-dsRNA cDNA clones would also facilitate efforts to define the role of specific viral gene products in modulating virulence and fungal gene expression.

The introduction of an artificial cDNA intermediate into the replication cycle of an HAV dsRNA could potentially have a very significant impact on current efforts to restore the American chestnut as a valuable forest species. Although transmissible hypovirulence has been shown to effectively control chestnut blight in Europe, attempts to apply this biological control strategy to North American forest ecosystems have met with limited success primarily due to problems associated with poor dissemination of the introduced hypovirulent strain (see Anagnostakis, 1982; MacDonald and Fulbright, 1991). It is generally accepted that the vegetative incompatibility system that governs the ability of different C. parasitica strains to undergo anastamosis can have a considerable influence on the spread of the hypovirulence phenotype. Since the HAV dsRNA responsible for the phenotype is transmitted only by anastomosis, an introduced hypovirulent strain can convert only those virulent strains in the population that are of the same or closely related vegetative compatibility (VC) group. If the number of different VC groups is low, as appears to be the case in Europe (Anagnostakis et al., 1986), a significant portion of the virulent strain can convert only those virulent strains in the population can be converted to hypovirulence by the introduction of hypovirulent stain s representing several different VC groups, i.e., few barriers to vegetative spread of the HAV dsRNA will exist in such a population. In contrast, if the VC structure of the virulent C. parasitica population is complex, as is the case in the eastern deciduous forest in North America (Anagnostakis et al., 1986), considerable barriers exist to vegetative dissemination. In this context, by introducing a single genetically engineered hypovirulent strain that contains integrated cDNA copies of L-dsRNA, we can obviate the barriers to vegetative dissemination imposed by the vegetative incompatibility system. Since sexual incompatibility in C. parasitica is homogenic at a single mating type locus (Anagnostakis 1984), barriers to the spread of the integrated L-dsRNA cDNA copy through the population by sexual crossing would be limited. Thus, the integrated L-dsRNA genetic information could be transmitted to a vegetatively incompatible strain by mating. Nuclear inheritance of the integrated L-dsRNA cDNA is followed by resurrection of the cytoplasmic L-dsRNA form in the progeny and subsequent vegetative dissemination through all VC groups represented in the progeny population.

The existing L-dsRNA cDNA clone can be subjected to genetic manipulations to produce hypovirulent fungal strains that are more effective biocontrol agents. Transformation of a virulent C. parasitica strain with a cDNA copy of ORF A resulted in suppressed sporulation (Choi and Nuss 1992). By appropriately mutating ORF A within the context of the infectious L-dsRNA cDNA clone, a hypovirulent strain can be engineered to exhibit an increased asexual sporulation capacity, thus resulting in an increased rate of dissemination of the hypovirulence phenotype. Additionally, every asexual spore would contain L-dsRNA genetic information either in a cDNA and dsRNA forms. This would contrast with the normal situation for strain EP713 where L-dsRNA is transmitted in approximately 40% of the conidia.

Since the surviving root systems of blight infested American chestnut trees continues to produce sprouts throughout its natural range (Anagnostakis, 1982), the release of improved genetically engineered hypovirulent C. parasitica strains could significantly contribute to the restoration of this once important forest species. Specific means of treatment will take into account potential alterations in host range, ecological fitness, meiotic stability of the integrated L-dsRNA genetic information and mitotic stability of the resurrected L-dsRNA.

Finally, the availability of a full-length cDNA clone of the HAV L-dsRNA provides an opportunity to expand this form of biological control to other pathogenic fungi.

EXAMPLE 3

Materials and Methods Fungal strains and growth conditions

C. parasitica strains EP155 (virulent, dsRNA-free, ATCC #38755) and EP713 (isogenic to EP155, hypovirulent, contains dsRNA, ATCC #52571) were maintained as described previously (Hillman et al., 1990). Inoculum for induction experiments was prepared by growing cultures in potato-dextrose broth (PDB, Difco) at 25 degrees C., in the dark, without shaking. Once the cultures reached stationary phase, mycelial clumps were disrupted by grinding with a Polytron (Kinematica) and the cultures were diluted with one volume of PDB and stored at 4 degrees C. Cultures used to examine the induction of laccase mRNA accumulation were initiated by inoculating 50ml of PDB in 250 ml Delong flasks with 1/20th volume of inoculum. Growth conditions were as described for the inoculum except that the growing hyphae were dispersed by gently pipetting twice a day. After 40 h to 48 h, a zero time sample was removed and cycloheximide was added to a final concentration of 3 mM from a 3mM stock solution prepared in ethanol. An equivalent volume of ethanol was added to uninduced cultures. The flasks were swirled gently and incubated as described above.

Identification and characterization of the gene encoding laccase

The probe used to screen the C. parasitica genomic library was generated by polymerase chain reaction (PCR) amplification of a 720bp fragment corresponding to the 240 C-terminal amino acid coding domain of N. crassa laccase (Germann et al., 1988). Template DNA was prepared from N. crassa (FGSC #2489) obtained from the Fungal Genetics Stock Center, Kansas City, Kans. PCR (Saiki et al., 1988) was performed with reagents from the GeneAmp kit (Perkin-Elmer-Cetus) for 30 cycles with the following parameters: denaturation for 1.5min at 94 degrees C., annealing for 2min at 62 degrees C., extension for 3min at 72 degrees C. The PCR product was treated with T4 DNA polymerase (Sambrook et al., 1989), cloned into the SmaI site of pUC19 and subjected to sequence analysis before use. All sequence analyses were performed by the dideoxy termination method (Sanger et al., 1977) using Sequenase reagents (US Biochemical Co.). Library screening, subcloning and other routine procedures were performed according to standard protocols (Sambrook et al., 1989).

For primer extension analysis, a 17 nucleotide oligodeoxynucleotide, complementary to the laccase gene sequence at map positions 125 to 141, was 5'-end-labelled with [$^{32}$P] ATP by T4 polynucleotide kinase (Sambrook et al., 1989). One pmol of the labelled primer was hybridized with 0.9 mg of poly(A)$^+$RNA in 10 ml of a solution containing 0.2M NaCl and 5 mM PIPES, pH6.4. The mixture was heated at 65 degrees C. for 3 min and transferred to 50 degrees C. for 2 h. The reaction mixture was added to 90 ml of a solution containing 50 mM Tris-HCl, pH8.3, 10 mM DTT, 6 mM $MgCl_2$, 0.5 mM each deoxynucleotide triphosphate and 25 mg/ml Actinomycin D. cDNA synthesis was initiated by the addition of 10 U of avian myeloblastosis reverse transcriptase (Promega). Following incubation at 42 degrees C. for 1 h, the reaction mixture was precipitated with ethanol. The pellet was suspended in standard sequencing sample buffer, heat denatured and analyzed on an 8% polyacrylamide/7M urea sequencing gel.

The precise intron/exon junctions were located by sequence analysis of PCR-amplified laccase cDNA generated from an EP155 cDNA library or poly(A)$^+$mRNA. cDNA was synthesized as described by Xu et al. (1987) without prior treatment with methylmercuric hydroxide. Appropriate sets of primers (sequences available upon request) were employed to amplify laccase cDNA sequences under the following conditions: denaturation at 94 degrees C. for 1.0 min, annealing at 50∞C. for 30 sec and extension at 72 degrees C. for 30-sec for a total of 30 cycles. The PCR products were subcloned into pUC19 for sequence analysis.

Nucleic acid preparation and analysis

Total nucleic acids were prepared from *C. parasitica* cultures by the method of Borges et al., (1990) with minor modifications. Liquid grown mycelium (1–2 gm) was harvested, blotted dry and powderized in liquid nitrogen with a mortar and pestle. The mycelial powder was transferred to a 50 ml polypropylene Corning centrifuge tube containing 15 ml of cold buffer (4 mM spermidine, 10 mM EDTA, 0.1M NaCl, 0.5% SDS, 10 mM freshly added b-mercaptoethanol and 40 mM Tris HCl, pH8.0), and shaken vigorously. The mixture was extracted twice with phenol/chloroform/isoamyl alcohol (25/24/1) and once with chloroform. The aqueous phase was amended with 0.1 vol of 3M sodium acetate (pH5.5) and nucleic acids were precipitated by incubating on ice for 10 min after addition of 2 vol of cold ethanol. The precipitate was collected by centrifugation at 10,000 rpm in a Beckman JS-13 rotor for 10 min, rinsed with 75% ethanol and dissolved in TE buffer (10 mM Tris-HCl, pH7.5, 1 mM EDTA). These preparations were used for Southern hybridization experiments after digestion with appropriate restriction endonucleases.

*C. parasitica* RNA was prepared for Northern analysis by a method originally developed for *N. crassa* (Yarden and Yanofsky, 1991) following several modifications. Mycelia was harvested from liquid culture by gentle vacuum filtration through Miracloth (Calbiochem) and excess liquid was removed by blotting. The drained mycelial pads were inserted into 1.5 ml screw top microcentrifuge tubes containing 0.5 gm of 0.5 mM Zirconium beads, 350 ml of water saturated phenol, and 500 ml of extraction buffer [150 mM sodium acetate, pH5.0, 100 mM LiCl, 4% SDS, 10 mM EDTA and 20 mM b-mercaptoethanol (adapted from Lucas et al., 1977)]. The tubes were immediately shaken for 1 min in a Mini Bead Beater (Biospec Products) set at high speed, allowed to cool and shaken a second time for 2 min at low speed. 350 ml of chloroform-isoamyl alcohol was added and the samples were shaken an additional two min at low speed. Following centrifugation to separate the phases, the phenol phase was re-extracted with 250 ml of extraction buffer. The aqueous phases were then combined and extracted with phenol-chloroform until no interface was present; the final aqueous phase was then extracted once with chloroform. RNA was precipitated by adding ⅓ vol of 8M LiCl and incubated overnight at 4 degrees C. The precipitate was recovered by centrifugation, washed with 80% ethanol, thoroughly drained, resuspended in 2 mM EDTA and stored at −70 degrees C. RNA concentrations were determined photometrically. Samples containing 15 mg of RNA were denatured, subjected to electrophoresis through a formaldehyde-1.5% agarose gel and transferred to a nylon membrane (Gene Screen Plus, DuPont). Blots were hybridized with probes specific for *C. parasitica* laccase, actin, b-tubulin and glyceraldehyde 3-phosphate dehydrogenase (gpd-1) transcripts in four independent, sequential hybridization reactions under stringent conditions as specified by the membrane manufacturer.

Nucleotide sequence accession number

Nucleotide sequence data reported in this paper have been submitted to the GenBank data base and were assigned accession number M73257.

Identification and characterization of the *C. parasitica* laccase gene

Screening of a *C. parasitica* genomic DNA library with a 720 bp PCR amplicon corresponding to the 240 amino acid carboxyl-terminal coding domain of the *N. crassa* laccase gene resulted in the identification of 12 prospective positive clones. Of these, four clones (lambda LAC1, lambda LAC12, lambda LAC14, lambda LAC15) were further characterized and shown, by restriction- and Southern-hybridization analysis, to contain independent overlapping inserts. An overview of the *C. parasitica* laccase gene organization, as revealed by sequence analysis of a series of contiguous subclones extending in both directions from the region that was hybridized to the *N. crassa* specific probe, is presented in FIG. 1.

Two transcription start sites for the *C. parasitica* laccase gene were identified by primer extension experiments. A canonical TATA box was identified 42 nt upstream of the first transcription start site and the sequence between the two elements was found to be pyrimidine rich (31 of 42 residues). This is similar to the organization of the *N. crassa* laccase gene in which a TATA box motif was found 42 nt upstream of the transcription start site and the intervening sequence contained 29 pyrimidine residues. In contrast to the *N. crassa* laccase gene, the *C. parasitica* laccase gene contained a CCAAT motif 64 nt upstream of the first transcription start. The first ATG codon located downstream of the identified transcriptiontart sites (map positions 86–88) also constituted the initiation codon of the predicted laccase coding region based on amino acid sequence similarities with the predicted *N. crassa* laccase amino acid sequence (Germann et al., 1988). The nucleotide sequence context of this ATG codon, ATCAAT<u>ATG</u>C, is similar to the consensus sequence, $A_G$TCA$^A$CA<u>ATG</u>G, derived for favorable translation initiation of *N. crassa* genes (Roberts et al., 1988).

The predicted *C. parasitica* laccase coding domain consisted of 592 codons, including the termination codon at map positions 2864–2866, and contained a total of 12 introns. By contrast, the *N. crassa* laccase gene was reported to contain a single intron (Germann et al., 1988) that upon inspection was found to correspond to the second intron found in the *C. parasitica* laccase gene. The presence and exact boundaries of the predicted introns were confirmed by sequence analysis of PCR-amplified laccase cDNA generated from a *C. parasitica* strain EP155 cDNA library or poly(A)$^+$mRNA. Intron sizes ranged from 55 to 214 nucleotides, comparable to that reported for other fungal genes (Germann et al., 1988; Roberts et al., 1988). A survey of 17 introns compiled from three *C. parasitica* genes; the genes for laccase (lac-1, this study), glyceraldehyde 3-phosphate dehydrogenase (gpd-1) (Choi and Nuss, 1990) and endothiapepsin (epn-1, G.H.C., R. Shapira, and D.L.N.), revealed the conserved sequences GT$^A$G$^A$GGT and $^G$TAG for the 5' and 3' splice sites, respectively. Additionally, an internal consensus sequence CT$^G$AAC, which may be involved in lariat formation (Langford et al., 1984), was identified 6–24 nucleotides upstream of the 3' splice sites. These consensus sequences are in agreement with those found for other fungal introns (Roberts et al., 1988).

The *C. parasitica* laccase polyadenylation site was mapped to position 3226 also by sequence analysis of PCR amplified laccase cDNA. In this case, the 3' primer contained nineteen 3'-terminal T-residues and the 5' primer was complementary to map positions 1986–2002. There was no evidence of a typical polyadenylation signal, AATAAA (Proudfoot and Brownlee, 1976), in the region upstream of the polyadenylation site, a situation common to many fungal genes. However, two pyrimidine-rich regions were observed at map positions 2949–3008 and 3018–3066. Similar thymidine- and cytosine-rich regions were also found in the 3' noncoding region of the *N. crassa* laccase gene (Germann et al, 1988).

Comparison of the predicted amino acid sequences for the *N. crassa* and *C. parasitica* laccases revealed a 73% similarity with a 57% level of identity. Regions of high similarity include four domains considered to contain copper-binding ligands that are conserved among a number of multicopper oxidases (Messerschmidt and Huber, 1990). These regions are highly conserved in all four fungal laccases for which sequence information is available and share considerable sequence similarity with multicopper oxidases from plant and animal sources. The high level of conservation for these regions among the fungal laccases contrasts with the overall level of amino acid similarity, e.g., comparison of the *C. parasitica* laccase and the *A. nidulans* laccase1 amino acid sequences (Aramayo and Timberlake, 1990) revealed values of 51% similarity and only 28% identity.

Comparison of the predicted *N. crassa* laccase amino acid sequence with that of the purified mature form of the protein revealed evidence for both N-terminal and C-terminal processing (Germann et al., 1988). Although the *N. crassa* laccase sequence contains a putative signal peptide sequence, additional processing events appear to result in the removal of a total of 49 N-terminal residues from the precursor protein (Germann et al., 1988). Moreover, there is evidence for the processing of 13 residues from the C-terminus of the precursor. Interestingly, the predicted *C. parasitica* laccase sequence is 28 residues shorter than that predicted for the *N. crassa* laccase, and gaps in the alignment of the two sequences fall within these terminal domains. While the N-terminal portion of the *C. parasitica* sequence contains the hallmarks of a signal peptide (von Heijne, 1986), i.e., a positively charged residue at position 6 followed by a hydrophobic core region as revealed by hydropathy analysis (data not shown) and several potential dipeptide cleavage sites, it also contains two large alignment gaps, comprising 15 residues, within the region corresponding to the 49 residues that are processed from the N-terminal portion of the *N. crassa* laccase sequence. Additionally, the *C. parasitica* laccase sequence lacks a sequence corresponding to the 13 residue oligopeptide that is processed from the C-terminus of *N. crassa* laccase. These dissimilarities suggest that different pathways may be involved in the post-translational processing of these related enzymes. A comparison of the processing pathways for the laccases from these two ascomycetes may provide insights into general mechanisms involved in post-translational modification and secretion of fungal proteins.

Laccase gene expression

Southern blot analysis was performed on genomic DNA of the isogenic virulent/hypovirulent strains EP1 55/EP713. Identical patterns consisting of anticipated 3.3 kbp and 1.3 kbp bands, corresponding to the 5' and 3' portions of the laccase gene, were observed for both strains. Combined, the two fragments span the laccase gene from 1976 nucleotides upstream of the first transcription start site through intron 12 (map positions −1976 through 2669). This result indicates the absence of closely related genes in the *C. parasitica* genome and confirms that both strains EP155 and EP713 contain the same structural gene. Additional Southern analysis indicated that there was no apparent structural rearrangement of the laccase gene due to the presence of the HAV-dsRNA and that the laccase gene is likely present as a single copy gene in each strain.

The level of accumulation appeared to be influenced by a variety of conditions including the culture medium, the age of the culture and exposure to light, while laccase mRNA accumulation was generally found to be substantially lower in strain EP713 than in EP155.

As shown in FIG. 6, addition of 3 mM cycloheximide to cultures of the virulent *C. parasitica* strain EP155 resulted in a time-dependent increase in the accumulation of a ~2.3 kb RNA species corresponding to laccase mRNA. An increase in band intensity was evident by 6 h after cycloheximide addition and was found to reach a level of approximately 15–20 fold by 24 h. Although some variability was observed in the uninduced level of laccase mRNA and, consequently, the final magnitude of induction, the addition of 3 mM cycloheximide consistently resulted in a significant increase in laccase mRNA accumulation.

To test whether the induction of laccase mRNA accumulation was selective, or whether the results reflected a general increase in mRNA accumulation, blots were re-hybridized with probes specific for other *C. parasitica* mRNAs. These included probes for mRNAs that encode two structural proteins, b-tubulin and actin, and an mRNA encoding the highly expressed protein, glyceraldehyde 3-phosphate dehydrogenase. The levels of b-tubulin and actin mRNAs (1.9 kb and 1.8 kb, respectively) were found to change little during the 24 h incubation period with the small variation observed most likely being related to differences in sample loading. The level of gpd-1 mRNA (1.5 kb) also remained relatively stable over the incubation period, exhibiting a slight increase in accumulation by the 24 h time point.

Laccase activity has been shown to be associated with pigment production in several fungi. For example, laccase is probably involved in the production of a brown pigment during fruiting body formation in the basidiomycete *Schizophyllum commune* (Leonard, 1971). A role for laccase in the production of the green pigment associated with spores of the ascomycete *Aspergillus nidulans* has been confirmed by genetic means (Clutterbuck, 1972). In this regard, hypovirulent *C. parasitica* strain EP713 exhibits both reduced pigmentation and reduced laccase activity. Within the context of host-pathogen interaction, laccase could potentially contribute to pathogen-mediated degradation of lignified zones (Lewis and Yamamoto, 1990) generated by the host as a physical defense mechanism. It is well established that hypovirulent *C. parasitica* strains are deficient in their ability to form the deep necrotic cankers associated with infection by virulent strains (Hebard et al., 1984, and reviewed by Griffin, 1986).

References

1. S. L. Anagnostakis, *Science* 215, 466 (1982).
2. M. K. Roane, G. J. Griffin and J. R. Elkins, in *Chestnut Blight, Other Endothia Diseases and the Genus Endothia*, (APS Press., St. Paul, Minn., 1987) p. 53.

3. G. J. Griffin, *Hort. Rev.* 8, 291 (1986).
4. W. L. MacDonald and D. W. Fulbright, *Plant Disease*, 75, 656 (1 991).
5. J. Grente, C.R. *Acad. Agt Fr.*, 51, 1033 (1965).
6. J. Grente and S. Berthelay-Sauret, *Proceedings of the American Chestnut Symposium*, W. L. MacDonald, F. C. Cech, J. Luchok, C. Smith, Eds. (West Virginia University Press, Morgantown, 1978), pg. 75.
7. N. K. Van Alfen, R. A. Jaynes, S. L. Anagnostakis, P. R. Day, *Science* 189, 890 (1975).
8. P. R. Day, J. R. Dodds, J. E. Elliston, R. A. Jaynes, S. L. Anagnostakis, *Phytopathology*, 67, 1393 (1977).
9. G. H. Choi, R. Shapira, D. L. Nuss, *Proc. Natl. Acad. Sci. USA* 88, 1167 (1991).
10. G. H. Choi, D. M. Pawlyk, D. L. Nuss, *Virology* 183, 747 (1991).
11. R. Shapira, G. H. Choi, D. L. Nuss, *EMBO J.* 10, 731 (1991).
12. R. Shapira and D. L. Nuss, *J. Biol. Chem.* 266, 19419 (1991).
13. E. V. Koonin, G. H. Choi, D. L. Nuss, R. Shapira, J. C. Carrington, *Proc. Natl. Acad. Sci. USA* 88, 10647 (1991).
14. K. W. Buck, in *Fungal Virology*, K. W. Buck, Ed. (CRC Press, Boca Raton, Fla., 1986), pp. 1–84.
15. R. B. Wickner, *FASEB J.* 3, 2257 (1989).
16. M. El-Sherbeini, D. J. Tipper, D. J. Mitchell, K. A. Bostian, *Mol. Cell. Biol.* 4, 2818 (1984).
17. B. I. Hillman, R. Shapira, D. L. Nuss, *Phytopathology* 80, 453 (1 990).
18. M. Taniguchi, C. Palmieri, C. Weissman, *Nature* (London) 274, 223 (1978).
19. V. R. Racaniello and D. Baltimore, *Science* 214, 916 (1981).
20. R. K. Saiki, et al., *Science* 239, 487 (1988).
21. D. Rigling, U. Heiniger, H. R. Hohl, *Phytopathology* 79, 219 (1989).
22. L. Roux, A. E. Simon, J. J. Holland, *Adv. Vir. Res.* 40, 181 (1991).
23. D. Rigling, N. K. Van Alfen, *J. Bact.* 173, 8000 (1991).
24. C. E. Carpenter et al., *Mol. Plant-Microbe Inter.* 4, 55 (1992).
25. G. H. Choi, T. G. Larson, D. L. Nuss, *Mol. Plant-Microbe Inter.* (in press).
26. S. L. Anagnostakis, B. Hau and J. Kranz, *Plant Disease* 70, 536 (1986).
27. Anagnostakis, S. L. (1982) *Science* 215, 466–471.
28. Anagnostakis, S. L. (1987) *Mycologica* 79, 23–37.
29. Anagnostakis, S. L. (1984) In Jennings, D.H. and Rayner, A.D.M. (eds). *The Ecology and Physiology of the Fungal Mycelium*, Cambridge University Press, Cambridge, pp.353–366.
30. Anagnostakis, S. L. (1990) *Forest Science* 36, 113–124.
31. Anagnostakis, S. L. and Day, P. R. (1979) *Phytopathology* 69, 1226–1229.
32. Bavendamm, W. (1928) Z. *Pflanzenkrank. Pflanzenkschutz* 38, 257–276.
33. Choi, G. H. and Nuss, D. L. (1990) *Nucleic Acids Res.* 18, 5566.
34. Choi, G. H., Shapira, R. and Nuss, D. L. (1991a) *Proc. Natl. Acad. Sci.* USA 88, 1167–1171.
35. Choi, G. H., Pawlyk, D. M. and. Nuss, D. L. (1991b) *Virology* 183, 747 –752.
36. Churchill, A. C. L., Ciuffetti, L. M., Hansen, D. R., Van Etten, H. D. and Van Alfen, N. K. (1991) *Curr. Genet.* 17, 25–31.
37. Cullen, D., Leong, S. A, Wilson, L. J. and Henner, D. J. (1987) *Gene* 57, 21–26.
38. Day, P. R., Dodds, J. A., Elliston, J. E., Jaynes, R. A. and Anagnostakis, S. L. (1977) *Phytopathology* 67, 1393–1396.
39. Elliston, J. E. (1978) In MacDonald, W. L., Cech, F. C., Luchok, J. and Smith, H. C. (eds) *Proceedings of the American Chestnut Symposium*, West Virginia University Press, Morgantown, pp.95–100.
40. Elliston, J. E. (1985) *Phytopathology* 74, 151–158.
41. Grente, J. and Berthelay-Sauret, S. (1978) In MacDonald, W. B., Cech, F. C., Luchok, J. and Smith, H. C. (eds), *Proceedings of American Chestnut Symposiuym*, West Virginia University Press, Morgantown, pp.30–34.
42. Hillman, B. I., Rae, B., Tartaglia, J. and Nuss, D. L. (1989) In *Molecular Biology of Plant Pathogen Interactions, Proc.* UCLA Symposium 101, 59–70.
43. Hillman, B. I., Shapira, R. and Nuss, D. L. (1990) *Phytopathology* 80, 950–956.
44. Jaynes, R. A. and Elliston, J. F. (1980) *Phytopathology* 70, 453–456.
45. Koonin, E. V., Choi, G. H., Nuss, D. L., Shapira, R. and Carrington, J. C. (1991) *Proc. Natl. Acad. Sci.* USA (in press).
46. Rigling, D., Heiniger, U. and Hohl, H. R. (1989) *Phytopathology* 79, 219–223.
47. Shapira, R. and Nuss, D. L. (1991) *J. Biol. Chem.* (in press).
48. Shapira, R., Choi, G. H. and Nuss, D. L (1991) *EMBO J.* 10, 731–739.
49. Van Alfen, N. K., Jaynes, R. A., Anagnostakis, S. L., and Day, P. F. (1975) *Science* 189, 890–891.
50. Rae, et al. (1989) *EMBO J.* 8:657–663.

We claim:

1. A cDNA polynucleotide having the sequence of FIG. 1, or any fragment thereof which is an open reading frame.

2. A cDNA polynucleotide having the sequence from about nucleotide 496–498 to about nucleotide 2362–2364 of FIG. 1.

3. A cDNA polynucleotide having the sequence from about nucleotide 2364 to about nucelcotide 11859–61 of FIG. 1.

4. A vector suitable for expression in fungi which contains a polynucleotide of claim 1.

5. A vector suitable for expression in fungi which contains a polynucleotide of claim 2.

6. A vector suitable for expression in fungi which contains a polynucleotide of claim 3.

7. An RNA having a sequence which is complimentary to the cDNA sequence of FIG. 1 or any fragment thereof which is an open reading frame.

8. An RNA having a sequence which is complimentary to the cDNA sequence of FIG. 1 or any fragment thereof which is an open reading frame.

9. An RNA having a sequence which is complimentary to the cDNA sequence of FIG. 1 or any fragment thereof which is an open reading frame.

10. The RNA of claim 7 wherein said RNA is a dsRNA.

11. The RNA of claim 8 wherein said RNA is a dsRNA.

12. The RNA of claim 9 wherein said RNA is a dsRNA.

13. A fungus or fungal spore or parts of either having integrated therein the cDNA of claim 1.

14. A fungus or fungal spore or parts of either having integrated therein the cDNA of claim 2.

15. A fungus or fungal spore or parts of either having integrated therein the cDNA of claim 3.

16. A fungus or fungal spore or parts of either having integrated therein the RNA of claim 7.

17. A fungus or fungal spore or parts of either having integrated therein the RNA of claim 8.

18. A fungus or fungal spore or parts of either having integrated therein the RNA of claim 9.

19. A *C. parasitica* fungus or fungal spore having integrated therein the cDNA of claim 1.

20. A *C. parasitica* fungus or fungal spore having integrated therein the cDNA of claim 2.

21. A *C. parasitica* fungus or fungal spore having integrated therein the cDNA of claim 3.

22. A *C. parasitica* fungus or fungal spore having integrated therein the RNA of claim 7.

23. A *C. parasitica* fungus or fungal spore having integrated therein the RNA of claim 8.

24. A *C. parasitica* fungus or fungal spore having integrated therein the RNA of claim 9.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 12752 base pairs
        ( B ) TYPE: nucleic acid
        ( C ) STRANDEDNESS: single
        ( D ) TOPOLOGY: linear ( i i ) MOLECULE TYPE: cDNA (iii) HYPOTHETICAL: NO (iv) ANTI-SENSE: NO (vi) ORIGINAL SOURCE:
   (A) ORGANISM: Endothia parasitica (Cryphonectria parasitica)
   (B) STRAIN: EP713

(xi) SEQUENCE DESCRIPTION: SEQ ID NO:1:

| | | | | | | |
|---|---|---|

-continued

```
CTGACTTCGG  TCAGGGACAA  GCTCGACCCC  GGCCGCGCGT  TTGGTTACGT  GCAGGCTGCG  2160
GTTGCGCAGG  GCATGTCCGA  CTTCCGGAGG  GCAAAGCGGG  CATTGGCGAT  CGTCGCCAAG  2220
CCCGTAATCC  GGAACATCCG  TGACCCCTAT  GAGCACGGGT  TTGTCAAGCG  AGATGGTAAG  2280
CTTCGCCATT  CTCGCGACGC  ATTTAATAAG  AAGCTGCGTA  CAAAGGCCGT  GGCCGCCACG  2340
AAGGTCCACA  AAATAAAATT  TTAATGTATA  AGGAAGCCGA  ACGACCTATT  GAAGTGTGGC  2400
GAACACAGGT  CATGGACGGG  CCAACATGGA  CTGCCCTTTC  TGAGTCGTGC  AGGGACAGGT  2460
TGTTCTTTGC  ATCCGGGGAA  GGTGGTGAGC  ACATGACGCT  CGATATCATC  AGCCTGATT   2520
CGTACACCAA  GATACGCTTA  TTTCGCAGCG  GTCGGTTCGA  GGTGTCGGTT  GACGGAAAGA  2580
GTTTTGGCCA  GGGCGGCAAC  CGTTATAGAT  TCGTCTTTCG  CTATGACTCT  TTGCTGTCGA  2640
CACCTTTTGG  ATATCCTGCC  GAGGACAAGG  AAATAGCGCT  TCAGGATTAC  AATCACAAGC  2700
AGTTGCTGGG  TGAGATGTTC  TTGAAGCTTC  CTGACTCCTA  TGTTGACGGG  AGACCGATCG  2760
CTGAGGCTTT  CTTTCGTTAC  GTTGACGACC  TGAAATGGGA  TGTCGGCGTG  TTCCGTGACC  2820
GCAGGTCGCT  AACGGAACTT  CATTTACCAG  CATCATCTGG  TTTAACAACT  GCACAAGTTT  2880
CGGTGGCCAA  ACTCGAATGG  CCGCCACTAC  CTATCATCCA  GGCCCAGCCG  ACAATACTAG  2940
CCGGTATCAT  TGACAACTTC  AAGATTGCT   TCCCCGTAAA  CGGGAAATGG  ATCTATGGTC  3000
AAGGGTTGTC  ATGGACCAGA  TACGATGGCG  ATGCCTCCGT  TCCAACCTCT  CTATTGTCCA  3060
ACCGACAGCA  CGCGAGGTTC  TGGAACGAGA  AGGACATCCC  CACCGGCCTG  AAGCTTTCAA  3120
AGGAAGGCTT  CATCAAGCTC  TGGGCCCAGA  AATCTCGCAA  GTGGCAGGAC  ACATGGCGA   3180
GATCGATAGG  ATTAAGTCAC  GAGGCCGCTG  TAGAGTTGGT  TCGTGCAACA  AGAGTGAACG  3240
AAGCAAAGCC  CCATCTCGTC  CCCATGGAAG  AGGCGAAAGA  GGCACCTAGG  CAGCAGCTTG  3300
TTCCTAGGCG  TTCAACTTTC  GTCGATAACC  ATGAGGAGGA  GGTTGAGATT  GACACCCTTC  3360
GGGTGCCGGT  CGAAGAGGGT  CGATGTTTCG  AGCTCTTGTT  CAATAATCAA  GTAACCCCTG  3420
CAATTTTCGA  CAAGAAGCCA  TTGCTTAAAG  ACGTCCTCGG  CGTGTTCGAA  GAGAATGTCT  3480
GCACGATGGA  CTCGCTCGAA  ATCAGTCACA  GTGACCAATG  CGTGCACATT  GTCGCTGGTG  3540
AAACCTTCCG  GAACTACGAT  GAAATCAAAG  CCGTTCTCGA  GGTCATTCTT  GAGAACGAGC  3600
CTGACATCCT  CGTTGGAGCT  GAAGAAGGTT  CAGTCGCTGA  TTATGTGAAA  GCGGGCAAAC  3660
ACTTCTTGTT  TGAAAACCAC  CAGTGGGTCA  GAAATGGGCT  CAAGCTAGCG  AAGGGTCTAG  3720
CTGAACCTGG  CCAAAGGGCC  AAAGATAATA  CCAACCCTTC  GACACCTAGG  CCGATTGAAG  3780
ACGCTGACTA  CATTCATCCT  TTTGACAACG  GACAGCCCCT  CCCGGGCAGG  TCCGACCAAT  3840
GGGTCAGCGG  CTTTGAAGTG  ACGAGGTTAC  GTCACCATGA  CGAAATGCCA  CACATTAGGA  3900
GTGTGAGGAA  CACGGGCATC  CATGGGCTAC  CTGGGGATTT  CTTGTCGAAT  TACCCTAGAC  3960
TGCCTACGCC  TGTATTTCAT  CGCCTCCGCG  ATTTGTGGGA  TGATGTCATC  GGCATACTGA  4020
TGAAGCTTGA  ATTCGGGGAC  AATTGTTCAC  CGGTGCTCAA  CGTGACTGCT  AATGCAGACT  4080
GGGTTCGGTC  AGAGACGACG  ATAAATTTTA  TCTCTGACCA  ACCCGGCAAG  GCTCAGTCAC  4140
GTCCTCGCGA  AGATGGGGGT  TTTGACATCC  TCGTTCCTTG  CAGGGGCATC  GCAACCCGAA  4200
GCATCAGGCT  TCTGCCTCTA  TTCATCAGAC  TGCCAAACCG  TTTCAGGGCC  GTGGCTTTGT  4260
TAAACGGTAG  GCAGTCTGAT  TATGACAATT  ATGGTTGGCC  AGTGTTCAAT  CCGGTCATCC  4320
CATTGCCTCA  GATGGACTCC  TTCTACGTGG  AGGCCGTCGC  CGCTGGCAGA  TCAATGTACC  4380
CACCTGGTTT  CCTCCTAGGT  AGGTATGACG  CACTAGAGTA  TCTAGTGCAC  ACTGCGACGG  4440
TGTATGGCGC  TGAGGAAGCC  TTCTTGCTTC  CGTTCACGCA  TCATGTGAGA  GTGTATCCCC  4500
```

```
CTCCCCGTCC   AGGGAGGGAG   ATTCCTTTCG   GCTCGTGGTG   CAAGAACTAC   AAGTTCGAAG   4560
CAGAAAGGTT   TTGGTATGAC   GCGGACTGGA   AACTGAGGGT   CCACGAAACC   AACCACGATT   4620
TTGACAGGTT   AATCGAAATA   ACAAAAACCT   GTCGCCGCAA   CCCCCCCGAA   GAAAACTTGC   4680
AAGCAAAACT   GGAGGACACC   GCGCGCAAGG   TGTGTAGTGT   ATGGCAATAT   AACATCATGA   4740
TCGCTTCATC   TGTCGCGTTT   CTAGTGCCAT   TATACTTCAC   ACTCTATGTG   CCGTACCTGC   4800
AATTCTACTT   GCATGTTGAC   CCAGGCGATT   ACATATTGCT   TCCACCGGTG   CTCTGGTTGG   4860
TCTGGACCAA   TCTTTGCTAC   GGCTACGCGT   GTGACGCCTG   GTGCCGTTTA   TTTTTCTTCG   4920
TAGAGGAGGC   GGGAAAGAAA   GAACTTGTCC   ATTCAAGTGA   GGAGTTTTCC   AGTGACCCGT   4980
CATCCACGCT   CTTGATCCCG   ACAATGGGAA   CAAGAGGAGA   TCACGTGCCA   CCACGGTTCT   5040
TCGCCAACAT   GGCGGTCCTC   GCAGGTGTCA   AGACCCATCT   CTTGAAACTG   CAGACTGCGA   5100
CGTACGGCGA   TTTGGAGAAC   CTCAAGAAAG   GGAAGCTCGG   AAGCTTGTTG   CCAGGCTATC   5160
TTCAGAACCA   TTACTCGGTG   CTGAGGGGTT   ACAAAGCCGC   GTTCACTCCG   CATGTCGAGC   5220
TTGACATGCC   GAACGCAACT   TCGTACAACT   TAGCACCGCC   TCGCAGCTAC   ATCAACAAGA   5280
TACGGTACCT   GACCGATGAA   AATCGGTCGG   GCGCCAGTAT   GATTGATCGC   GCTGTGACCT   5340
GGTTCGCCGA   AGAACTGGCA   GACACGTTCT   GGCCCGACTG   GCAAATTGGT   TGCCTTAGAG   5400
GTTGCAATTT   ACCGCGTTCC   GCGGATGGTG   TTTCCCTGAT   CACCAAACAA   CCCAACCTTA   5460
AAACAGGGAA   AATCGGATGG   CTACATGGCT   CCGCTGATCC   AGCTGTGGTG   CCTAAGGACA   5520
TCAGGGACAA   GTACCCCCTG   GTTCCGAACG   GTGACCACAA   CGAGATCTTC   AGGCATTATG   5580
ATAAGATTTA   CATGCCTGGT   GGAGCCGGTG   CCGTCCAAAC   CGCAATCGCT   TGTGGATGCG   5640
AAGTCGTCGT   CACAGACGTC   AACCTTGACA   GAGATTATCA   CACAATGCCT   ACGCAGAAAG   5700
ACTTTCACCA   ACCCTCCATA   CTGCCATACT   TCGCATGGCT   GTGGAGGCAA   GGGTTTGATG   5760
TTAAACTGCC   ACGCGTGTTG   CTCGTCATAG   GCTGGCTGAA   GTTTCATTAC   TCCATCCGCT   5820
ACAAGCATCT   GGAATTCGCC   GCTGACTTCG   TCATCAGGGC   TGGGTTGTTC   TGGTGGTATG   5880
GGTGCTTGCA   CCTACTACCA   TTCATGGCAG   CCGCGATCAT   GGCACCAAGG   TTCGTTAAGA   5940
AGTACTTGGT   TGGCATGGCG   TGGTTAACTG   AACCCGGTCT   CCTAATGCTG   AAGGCGCTGT   6000
GGCGTTTTCC   AATTTTCATG   GTCACCCCAA   GGTGGATGCT   GCCGTTCATT   GTAACGGTTT   6060
CGGTATACAA   TTGGTGGTGG   CCGTTATCCC   AAGACGGGCT   CAACTACGCG   AGCAAACGGT   6120
TTGAATTGAT   CTTCGAACCG   GTAACTCGGG   GTAAGCACAC   GTTTTCCTAC   CCATTCGGGC   6180
ACTGGTGTTT   GCGTGACACC   AACTCGATGA   TTGTTTACGA   AGGAAAATTT   GTCAACCCAA   6240
GTGAGACCTC   AATCGGGTCT   CCCTTCAAGT   TGTCGAAGTC   CGTTAGACCG   GTCCGACCTG   6300
GCGCAGTGTT   CCACCTGGTG   CCTTTCCACG   TCCAGAAGCT   TCTGGATTCA   ATGGATGAGG   6360
CACCACTACC   TTACAGCGCG   AATCACAATT   GCACGACCGT   GATCCTCAAG   GGGATCATGT   6420
ACCGTAGTGC   ACTAGGTTTT   GTATTCGCGT   ATATGGTTTC   GTGGGCGGTG   TACCTGGTCC   6480
TCCGGCCTCC   TCAAGCCGCG   GCTACCGTTT   ATCACTGGGT   GTATCCCGAG   CGATCGTGGG   6540
ACACATCAAG   GCTGTATCAT   CTGCTGCTGG   GTTTCGCAGC   AGGTGGCACG   GTGCCAATGG   6600
AAGTGATAGA   CGAAGAGCAC   GTTGAGGAAA   AGCCTTCGGT   TGCTGGTCAG   TCAGAGCCAG   6660
CCGCCGAAAT   CGACAATGAC   AAAATTTCTG   ACTATGACCA   AGAATGGTGG   GGGAGTCAAG   6720
ACAGTATTGA   CACAGTGGTT   AACGACCTGT   GTTACTTGCT   GTCCTTCCTG   AAAGATACGG   6780
CGATCCCTGA   AGAGGTCAAA   CTCGATGTAG   TCGAACTGGC   TTACACCCAG   CTTGTCCAGG   6840
ACGAAAAGGA   ACGCATACCA   GAACCGAAGG   GAACTAAGAT   TCTGGACATG   CCGAATTGGA   6900
```

```
AGCCTGGCAA CTGGGCCAAG TTAATAGACG AGACGCATCG GGTGCTCTCC CAGTTTACTC 6960
AATATACACC GCGAGTTCTC AACGAACTCG TCGTGTGGTT GAAAGGACTA GGGGAGAACC 7020
TCTATAGGGT CGCTGAACCC ATTCTTATGC TATTAGTACG TGCGATGAGA GCTGCCAAAT 7080
CCGTGAGTGA TCGTGCCACA CGTTCCGTAT ATCACTGCCT CTGCCATTGG CTAGACGTGA 7140
TGTATGGCGG CTCCGCCCCT ACCAGGGTGA AGACCGTGTG GGGACTCACA GGCCTGGTGG 7200
CTTCTGGCAT GACCAGTCAG AAAGCCATAC TCGCTCAGAA CATAGCAATG ATGGAATACC 7260
AGGGCAGAGG GAATTTCCTT GATGATTATG ACAACTTTGT CTCCAACATC AAGGAACCCG 7320
GGAAAGGACT ACCTGGTATA AACACCATCG GAGGGCCACA ACGACGTCCG ATTCGATACA 7380
AGAACCCTGT CATGTCTCAC CAGGCTGCCG AAATCTGTGG ATTGAAGCCT GGGGAGTATG 7440
AAGTGGATGA TAGGTATCAG GAAAGGATAA ACGATTACCT TGCGGAAGGG ATCCCGCAGG 7500
CAGTCGATGG CGTCCTCTTT GGAGACAGGA ATCCCGACAG GATCGCGCGA TCCATAAGCC 7560
GATATGAACC CGAATACTCT GGCTGTTCGC CTGAGGACAA GGCCTTGGTG GAGGATACCG 7620
CCAGGGCCAT GTTCGAACAA TGGCCAGAAG TGTTCGCCGA TCGAGACATC ATGCTCCCTA 7680
AAGGTGTAGA ACTTTACATC AAAGAGAAGT ACTCGGCGGG CACCCCGTTC ATAAGCTCGT 7740
TCTATAAGAG TAGAAAGGCT CTTAAGCAAG CTGGTGTCAT GGATGTGATC CGTAAAAACG 7800
CACTGGAGTG CATCAGTACC GGTAAATACC CTACGCAATT TTACCACGCG TTCGCGAAGT 7860
CACAAGCGGT TCCTGGCCAA CCTTTGTTGG CTCCCCGCAT GAAGGACTTG CGAACGGTGG 7920
TCTCCGAGGA TCTATCCGCT TACATGGTCG ACCAGATCTT TCAGATCGAG GCCAACAAGC 7980
GAATAACCTG GGAAACGTAC GGTGCCGGTT CTGGCATGCC TTTGTCACAA TCGATGGCTC 8040
GCATTTGGGA CGAGCTGCAT GATTTGAGGA AACGCGAAGG AGGGCAGTTC ATCATTGCTG 8100
ATGCGACTGC CTACGACTCA AACTGTAAAC CAGCATTGTT CCATGGGGCT GGCAAACTGG 8160
TTGAGTTAGG TTTCCAAAAT CATCCGAGTG GCAAAGGACG ACAATTCGCA CAAGTTGTCC 8220
AGTGCAAATT CGAGGCCATG CAAAATGCAT GGGTCATGGG GATAACCGAA CCTTCCTATA 8280
CCGCCTTGAC TTTCCACGTC CCTGACGTGG CGGTGAGGCA TGAACTGGAA TCCAAGTACC 8340
CTGCACACTT TGCGACGTTC AGCGAGCTTC TGGCTCACAA TAATGTGAAC GTCACTGAGT 8400
GGAAGAGGTT ATCTTGGGAG GAACGGAAAG CATGTGCTCG TGACATGCAG GCCGTTCCTG 8460
GCAAGGTTTT CCTTACCAAT GATCCAGCAT TGCGATTGCA AGGCTCGTCA TGGCAAGGTT 8520
CTTTCACCAC CGAACCCAAA AGGGACGAAT TCCGGAAATA CCAAACTTAT TTCTATGATT 8580
CGAAGGCGGC AATGAGAGAA GATATAAAGC GTATTGTCTT CGCCAATCGC GAAGTCATAT 8640
CCAACGTCCA CCACAAGAAC CGTGGTGGAG GCACTGGTCA GAGTGCCACT TCGTGGGACA 8700
ATACAGCTAC ATTCAAACTT GGCGTCATCA GCGCCTGGGC ACGCGCTACT GGTAAACCGC 8760
CCAAAGATTT CTTTTGTTCA AACAGGCTCT ACAATACGAG CGATGACACA GTGTGGTGGT 8820
CTAAGGACCT GTTATCCTCT GCCGAGGTTG ATCGCTTCAA GCAAGCTGCC GCCGATTTTG 8880
GCATCCTGCT TGAGATCGGG TCGACCAAGA AGATAACAGA AGTGGAATAC TTATCGAAGT 8940
TGCCACGTCG CCCAACCGCA GAAGATTCAG CGGACTATCG GGCATGGAGG CAGGGAAGGA 9000
TCGAGAACAT GCGATCCTCA GGCCGGTTCA GTGAAGAGCA GCTTCTCTCC ATTGAACGCG 9060
AGCAACTACC TCAATTCCTG ATGGTCCAGA ACCCCACGGC TATTCTAATG CGAAGGACTG 9120
CTTTCCGTTA TTATCAGAGC AGTCCCTCGA AGTTCCTGTA CACCTCGTGT GAACGGGGTG 9180
CCGGTCACGC ACTCGTGACG GCATTCCAGC CCGCACTGTA CAAGAGGTTC GCAATTGAGT 9240
ACGCCGAGGA CCTGAATCGT CTCTGCAAGG AGCACCACAT CAATCAGCGC TACGAGCTCG 9300
```

-continued

```
TCAGTCAACA AGATAGGATG AAGATGCAGG TTATAAACGT GAACCCGAAC TGGAAACGGA     9360
ACTTCAAGTT GTCACCAAGA CAAGAAGCAT TCCTTCGGTG GATCAGGCAG GCCAAGTTTC     9420
CATCTTATCG ACAAGTTCTA GACATACACC TCAGGATAAG GGATCCTGAC CCATCCGCGC     9480
ATGATCGCTT TATCGCCAAA CTGGATCGCG CTTGGCGCAA TCCAGATGAG GGGATCCGTG     9540
ATATAGTGGA CGGGGTGTAT CGCTACACGG ACATGATACC TGAGGAGTTT AAAAGGTTCA     9600
TGCCGTCTAC GGACATGCTG TATGCCGAGA ATCCGTGGCA CACTCACAAC CAGTATGTGG     9660
AGAAATTCAT ATACCTCAAG TTGCTGGAAA CCACGACCGT TGACGAGCTC ACGTTCGCCC     9720
AATTTGATGC CGTCGCTAAG GAGTCCCCTT ACGGCATCTG CATGAATACG ATAAAGTTCT     9780
GGGAAGACCT AAGAGACCCT GACTATCTGA AGGATCTCTT GGCCTCCGAG GCCATGATAG     9840
ATAAGGTGCG CATCTACCAA GGCATGACTG TCATCATCTC GGCCATGTAT TTCGCAATGC     9900
ATTGGGTCGA GCTGTTTATT CAGTCACTGT TCTTGATAGG GCCATTATAT AATCTATTCA     9960
TGTGGTCGTT CTGGGGATTG TCAAAAGTCT ACGGACTGGC GAACACGTTT TATTGGCATG    10020
GTAAAGCCCG CTCGAGCAGA GAAATCAGCT CGATCCTGCC AAGAGACCCA TACATGTGGT    10080
CTAAACGTTT CGTCAGCACG ATGGCTGATT TCATCCCTGA ACGATTTGCT CTCGGTATCG    10140
TTCCCGTGAC CTTGGTCTTG GATGGTCTCG CCGAGATCAT CGAAGTTCTA TTTGGGCGCA    10200
TGTGGAGACT GTTTGCGAAT CTGAAATCGG TAGGCACCGA CTTCAGTGAC GCACGATCTG    10260
GCAAATCGTT AAATGTGCCG TCCAATCCTT GGGCCGCGTA CGCCCACACG TACGCAACAA    10320
AAGCCATCGA GCACGGTCAC GTTACTGTAG CCGCAAAAAC CGCTTCCGGT AAGTCCACTT    10380
TCTTCCCCGC AGCGGTGTGG GCGGAGAGGA GGAACATCGG AATCAAGAAA CTGTGGATCG    10440
TTATGCCAAG GAAGATCCTC CGCGATAACT GGGAGATTCC ATTTGACATC CGATCTCAAA    10500
TCGTGAAACG GGGCAAAACA CTAGACCCAT CGGCCGATAT CTACGTGACC ACGTACGGAC    10560
ATTTCCGAAC GAGGATAGGT GGACTGGTCC CGAGGGACAA CCTGGTGTTC TTCGATGAGT    10620
TTCACGAAAT GGACGGTTTC ATGCTACAGG ACGTGGAAGA CTGGAAAGGA CCAACCATCT    10680
TCATGAGTGC AACTCCTGTT GCACTTCATG GAATGGCCGG CATCCCTTTT CTTGAGCCAA    10740
CACTGCCAAA GCGTTTCAAT CTTACCGTTT ACAAGGTTGA TTCCGATGAC GTGTTGGAAA    10800
TGTGGAACCG GGCTCGGAAT CAGTTTGCTG ATCAGCCCGA ATTGTTGGCC CGCCCAATGA    10860
TCATAGTCCC CACATATAAC GAACTCAAGA AGACGATTGC TGGATTGGAG AACTTGGACA    10920
GGTCTATCAC GTGGCATGAG GTGAGCAGTA ATAGCCCCT CGTGCCTAAG ACTGGTGGCC    10980
TCGTGTGCAC GCCATATGTA CAAACTGGCA TCGATATCAA ACCCGCGCCG TCGATCTTGA    11040
TCGACAGCGG CCGAGATGTC ATTGTGCATA AGGGTAGGCT AGTCACACCC CACCCCTATA    11100
CGGACGAGAA GACCAACGAA CAGAGGGTCA ATCGTGTCGG TAGGACGATG GATGGTGTGG    11160
TCATACAGCC GCAACTGGCT GGCACAGGCA ACCCTCCTGT CAAGTATCCT AGTGGGATTT    11220
TCTTTTCTTC AGAGTTAGTC GCGGGGCAGT ACAAGGTCCC CCGATTAACT AAAGTCAATG    11280
GTTGTGTCCA CCCGGAACTG CCGTACATGT CAATCAAGTA CACATCCGAG CTTTCAGACC    11340
CCGCTAAAGC AAGGGAGGAG GAACAAAGCG TGACGAAATC GCTCCTGTTT ATCCATCTCA    11400
TGGCATTGGC GGGCGTCAGG CAGTCCGAAT GGGCCTTGCG TTACAATCGA TACTTTGAAC    11460
TTCACCTTCC TTTCGGGGAA GATGAAGATC ATTTGGAGCG CATCTTAACG TCGGGTAAAC    11520
TGAGGTATGC TAACCACATA CCAGTTGACA TGGCCATGCA GTTGCTGGGC AACGGGCACG    11580
TTACATGGGG CATCGGTGGC GTCCCCACAA TAACGCGACC AAGATATCCT TGTGATGGGA    11640
TGTGGGTGGA GGATCCCTCC TCCCGTAAGT CATATGCGCA CAAGGTACTT CTACACCAGC    11700
```

```
GGGAACATGC  AGAGATCGGC  ATGTGGCAAG  CGCAGGTCAA  CGAGCTCAGA  GCCCAGAACC  11760

TTGCCCTTCA  GTCACAGCTG  AGATCAGCAT  GCACCCGAAG  AAGCACAGCA  GGTCGCATCT  11820

TACGACACAC  CCGTCCTCCG  GATATACCTG  TTTGCGGTTA  ACACAAACCG  CCTTCCATTT  11880

GTCATTTCCT  TTGTCCTTTC  CACGGGAGTA  GTGACCCCGT  GACACGCCAA  AACCAGCACC  11940

TGAAGTGGAT  AACTCAAGCC  TATGACATGG  TCACTGCCCG  TCAGTAAAGA  CGTTAACCCG  12000

GGAGCTGATT  CTGTTAACAG  CCGCACCGCG  AACGGTACGT  AGATTAAATC  TACGGTTTTC  12060

TGCCTCCTGA  GAGATTGGCA  GGGGAAACCC  GCTGAAGAGT  CCAGGACCGA  ACACGACCAC  12120

CATTCCGGCG  AATGGTTAGG  CCTCGGGAGA  TGCAATTGTG  CCTCATCACC  ACACCCACGT  12180

GACCAATGAG  ACCAACTCGC  AAAGGAGCAG  GAAACACAGT  GCAACTGTCG  GCCAGCAATA  12240

GGGCTAGAAA  TACTAAATAC  CTTTAACTTG  GTGGTAGGCG  TGTACCGAAC  GACCCCGGCC  12300

CAGAAGACCA  GGGCTGATGC  TTGTTAGGCA  ACGGCAATAA  GACCGAAGCA  AGCACAGAGA  12360

CTGGAAAAGT  AAGCCGGATC  CGTCGACGTA  GGATCGTCTA  CATGTTCAAG  AAATGGGCGA  12420

AAAGGGTTGC  CCGAAAGTAT  GGGCTACGCG  CTTCGTTGTA  AAGCTACCCA  TACAAACCC   12480

TTCGGCGCAC  TCACAACTGA  AATGTTAGTG  TTTCAACATC  TCAGGAGTTT  TAGTGTTACC  12540

GTCCTGCGCA  AGCAAAGATG  AGAACTATAC  CTTTGACAAC  AAAGGGTATA  GGGATCGGAA  12600

AGGCCGCTGC  AGTAGGATTC  AGACAAATAA  ATTTTCTCTT  GAAAATGTCC  GCCGTTTTCT  12660

TTTGTTGGCT  ATTCCCTTTC  ACCGTGCGTA  CGGTGGGAAG  AGAACAACAA  AGAAAAAAAA  12720

AAAAAAAAAA  AAAAAAAAAA  AAAAAAAAA   AA                                 12752
```

( 2 ) INFORMATION FOR SEQ ID NO:2:

( i ) SEQUENCE CHARACTERISTICS:
        ( A ) LENGTH: 622 amino acids
        ( B ) TYPE: amino acid
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Endothia parasitica (Cryphonectria
              parasitica)
        ( B ) STRAIN: EP713

( x i ) SEQUENCE DESCRIPTION: SEQ ID NO:2:

```
Met  Ala  Gln  Leu  Arg  Lys  Pro  Ser  Gln  Ser  Leu  Val  Leu  Ser  Glu  Ser
1                 5                        10                       15

Val  Asp  Pro  Thr  Thr  Val  Asp  Pro  Phe  Val  Ser  Val  Arg  Thr  Glu  Glu
               20                      25                       30

Val  Val  Pro  Ala  Gly  Cys  Ile  Thr  Leu  Trp  Glu  Tyr  Arg  Asp  Ser  Cys
              35                      40                       45

Gly  Asp  Val  Pro  Gly  Pro  Leu  Ser  His  Gly  Asp  Leu  Arg  Arg  Leu  Arg
     50                      55                       60

Thr  Pro  Asp  Gly  Val  Cys  Lys  Cys  Gln  Val  His  Phe  Glu  Leu  Pro  Thr
65                      70                       75                       80

Val  Leu  Lys  Ser  Gly  Ser  Thr  Gly  Thr  Val  Pro  Glu  His  Pro  Ala  Val
                    85                      90                       95

Leu  Ala  Ala  Phe  Ile  Gly  Arg  Pro  Arg  Arg  Cys  Ser  Leu  Glu  Gln  Arg
                   100                     105                      110

Thr  Lys  Glu  Leu  Asp  Ser  Arg  Phe  Leu  Gln  Leu  Val  His  Gly  Gly  Leu
               115                     120                      125
```

-continued

| | | | | | | | | | | | | | |
|---|---|---|---|---|---|---|---|---|---|---|---|---|---|
| Pro | Ala | Arg | Pro | Ser | Tyr | Met | Ile | Ala | Arg | Pro | Pro | Arg | Pro | Val | Arg |
| | 130 | | | | | 135 | | | | 140 | | | | | |
| Gly | Leu | Cys | Ser | Ser | Arg | Asn | Gly | Ser | Leu | Ala | Gln | Phe | Gly | Gln | Gly |
| 145 | | | | | 150 | | | | 155 | | | | | 160 | |
| Tyr | Cys | Tyr | Leu | Ser | Ala | Ile | Val | Asp | Ser | Ala | Arg | Trp | Arg | Val | Ala |
| | | | | 165 | | | | | 170 | | | | | 175 | |
| Arg | Thr | Thr | Gly | Trp | Cys | Val | Arg | Val | Ala | Asp | Tyr | Leu | Arg | Leu | Leu |
| | | | 180 | | | | | 185 | | | | | 190 | | |
| Gln | Trp | Val | Gly | Arg | Arg | Ser | Phe | Gly | Ser | Phe | Gln | Ile | Glu | Lys | Ser |
| | | 195 | | | | | 200 | | | | | 205 | | | |
| Ala | Val | Asp | His | Val | Tyr | His | Val | Val | Val | Asp | Ala | Glu | Tyr | Gln | Ser |
| 210 | | | | | 215 | | | | | 220 | | | | | |
| Glu | Gln | Asp | Gly | Ala | Leu | Phe | Tyr | Gln | Ala | Ile | Leu | Gly | Leu | Ala | Glu |
| 225 | | | | | 230 | | | | | 235 | | | | | 240 |
| Lys | Asp | Pro | Leu | Ala | Arg | Ile | Gly | Gly | Arg | Leu | Asn | Pro | Leu | Ala | Ala |
| | | | | 245 | | | | | 250 | | | | | 255 | |
| Glu | Phe | Ala | Pro | Gly | Ser | Ala | Leu | Arg | Val | Glu | Pro | Val | Thr | Pro | Gln |
| | | | 260 | | | | | 265 | | | | | 270 | | |
| Val | Thr | Arg | Arg | Lys | Gly | Ser | Thr | Arg | Met | Thr | Gly | Arg | Asp | Pro | Thr |
| | | 275 | | | | | 280 | | | | | 285 | | | |
| Ile | Val | Ser | Val | Gly | Lys | Val | Gly | Met | Ala | Ile | Thr | Ser | Ile | Gln | Asp |
| | 290 | | | | | 295 | | | | | 300 | | | | |
| Ala | Leu | Val | Ala | Thr | Glu | Leu | Arg | Asn | Val | Asn | Phe | Gly | Arg | Arg | Asp |
| 305 | | | | | 310 | | | | | 315 | | | | | 320 |
| Thr | Glu | Ala | Glu | Cys | Arg | Arg | Leu | Trp | Ala | Arg | Tyr | Glu | Val | Asn | Asp |
| | | | | 325 | | | | | 330 | | | | | 335 | |
| Tyr | Phe | Arg | Arg | His | Lys | Ala | Glu | Leu | Leu | Lys | Phe | Asp | Ala | Arg | Leu |
| | | | 340 | | | | | 345 | | | | | 350 | | |
| Arg | Ser | Arg | Met | Ala | Lys | Lys | Pro | Ala | Ser | Ser | Arg | Ala | Arg | Pro | Ser |
| | | 355 | | | | | 360 | | | | | 365 | | | |
| Asp | Ala | Lys | Ile | Gln | Cys | Ile | Gly | Trp | Arg | Asp | Arg | His | Leu | Leu | Pro |
| | 370 | | | | | 375 | | | | | 380 | | | | |
| Gln | Arg | Leu | Ala | Gly | Leu | Ser | Lys | Gln | Gly | Arg | Ser | Leu | Val | Trp | Ser |
| 385 | | | | | 390 | | | | | 395 | | | | | 400 |
| Arg | Phe | Ala | Thr | Ser | Asn | Ile | Arg | Arg | Lys | Thr | Pro | Pro | Cys | Val | Val |
| | | | | 405 | | | | | 410 | | | | | 415 | |
| Asn | Pro | Ser | Ala | Asp | Pro | Val | Val | His | Asn | Trp | Lys | Asp | Ser | Ala | Ala |
| | | | 420 | | | | | 425 | | | | | 430 | | |
| Leu | Ala | Val | Lys | Lys | Ile | Ala | Glu | Ala | Arg | Arg | Arg | Gln | Glu | Ile | Arg |
| | | 435 | | | | | 440 | | | | | 445 | | | |
| Ala | Ala | Ala | Tyr | Ala | Glu | Arg | Ala | Lys | Ala | Arg | Gly | Gln | Thr | Asn | Val |
| | 450 | | | | | 455 | | | | | 460 | | | | |
| Val | Ala | Ser | Ile | Ser | Glu | Ala | Ile | Glu | Thr | Thr | Leu | Arg | Arg | Asn | Lys |
| 465 | | | | | 470 | | | | | 475 | | | | | 480 |
| Thr | Arg | Phe | Ala | Leu | Asp | Gly | Leu | His | Leu | Ala | Ala | Ser | Ala | Ile | Val |
| | | | | 485 | | | | | 490 | | | | | 495 | |
| Thr | Thr | Arg | Leu | Arg | Ser | Trp | Asn | Gln | Glu | Glu | Ile | Arg | Ala | Gly | Arg |
| | | | 500 | | | | | 505 | | | | | 510 | | |
| Glu | Phe | Arg | Lys | Ser | Thr | Thr | Ser | Trp | Ile | Trp | Arg | His | Val | Pro | Ser |
| | | 515 | | | | | 520 | | | | | 525 | | | |
| Ser | Ile | Gln | Asp | Ala | Leu | Asn | Leu | Thr | Ser | Val | Arg | Asp | Lys | Leu | Asp |
| | 530 | | | | | 535 | | | | | 540 | | | | |
| Pro | Gly | Arg | Ala | Phe | Gly | Tyr | Val | Gln | Ala | Ala | Val | Ala | Gln | Gly | Met |
| 545 | | | | | 550 | | | | | 555 | | | | | 560 |

```
Ser  Asp  Phe  Arg  Arg  Ala  Lys  Arg  Ala  Leu  Ala  Ile  Val  Ala  Lys  Pro
               565                      570                           575

Val  Ile  Arg  Asn  Ile  Arg  Asp  Pro  Tyr  Glu  His  Gly  Phe  Val  Lys  Arg
               580                      585                           590

Asp  Gly  Lys  Leu  Arg  His  Ser  Arg  Asp  Ala  Phe  Asn  Lys  Lys  Leu  Arg
               595                      600                      605

Thr  Lys  Ala  Val  Ala  Ala  Thr  Lys  Val  His  Lys  Ile  Lys  Phe
     610                 615                      620
```

(2) INFORMATION FOR SEQ ID NO:3:

(i) SEQUENCE CHARACTERISTICS:
        (A) LENGTH: 3165 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Endothia parasitica (Cryphonectria parasitica)
        (B) STRAIN: EP713

(xi) SEQUENCE DESCRIPTION: SEQ ID NO:3:

```
Met  Tyr  Lys  Glu  Ala  Glu  Arg  Pro  Ile  Glu  Val  Trp  Arg  Thr  Gln  Val
1                   5                        10                      15

Met  Asp  Gly  Pro  Thr  Trp  Thr  Ala  Leu  Ser  Glu  Ser  Cys  Arg  Asp  Arg
               20                       25                      30

Leu  Phe  Phe  Ala  Ser  Gly  Glu  Gly  Glu  His  Met  Thr  Leu  Asp  Ile
          35                       40                      45

Ile  Gln  Pro  Asp  Ser  Tyr  Thr  Lys  Ile  Arg  Leu  Phe  Arg  Ser  Gly  Arg
     50                       55                      60

Phe  Glu  Val  Ser  Val  Asp  Gly  Lys  Ser  Phe  Gly  Gln  Gly  Gly  Asn  Arg
65                       70                      75                       80

Tyr  Arg  Phe  Val  Phe  Arg  Tyr  Asp  Ser  Leu  Leu  Ser  Thr  Pro  Phe  Gly
               85                       90                      95

Tyr  Pro  Ala  Glu  Asp  Lys  Glu  Ile  Ala  Leu  Gln  Asp  Tyr  Asn  His  Lys
               100                      105                     110

Gln  Leu  Leu  Gly  Glu  Met  Phe  Leu  Lys  Leu  Pro  Asp  Ser  Tyr  Val  Asp
          115                      120                     125

Gly  Arg  Pro  Ile  Ala  Glu  Ala  Phe  Phe  Arg  Tyr  Val  Asp  Asp  Leu  Lys
     130                      135                     140

Trp  Asp  Val  Gly  Val  Phe  Arg  Asp  Arg  Arg  Ser  Leu  Thr  Glu  Leu  His
145                      150                     155                      160

Leu  Pro  Ala  Ser  Ser  Gly  Leu  Thr  Thr  Ala  Gln  Val  Ser  Val  Ala  Lys
                    165                     170                     175

Leu  Glu  Trp  Pro  Pro  Leu  Pro  Ile  Ile  Gln  Ala  Gln  Pro  Thr  Ile  Leu
               180                      185                     190

Ala  Gly  Ile  Ile  Asp  Asn  Phe  Lys  Ile  Cys  Phe  Pro  Val  Asn  Gly  Lys
          195                      200                     205

Trp  Ile  Tyr  Gly  Gln  Gly  Leu  Ser  Trp  Thr  Arg  Tyr  Asp  Gly  Asp  Ala
     210                      215                     220

Ser  Val  Pro  Thr  Ser  Leu  Leu  Ser  Asn  Arg  Gln  His  Ala  Arg  Phe  Trp
225                      230                     235                      240

Asn  Glu  Lys  Asp  Ile  Pro  Thr  Gly  Leu  Lys  Leu  Ser  Lys  Glu  Gly  Phe
               245                      250                     255
```

```
Ile Lys Leu Trp Ala Gln Lys Ser Arg Lys Trp Gln Asp His Met Ala
            260                 265                 270
Arg Ser Ile Gly Leu Ser His Glu Ala Ala Val Glu Leu Val Arg Ala
            275                 280                 285
Thr Arg Val Asn Glu Ala Lys Pro His Leu Val Pro Met Glu Glu Ala
            290                 295                 300
Lys Glu Ala Pro Arg Gln Gln Leu Val Pro Arg Arg Ser Thr Phe Val
305                 310                 315                 320
Asp Asn His Glu Glu Glu Val Glu Ile Asp Thr Leu Arg Val Pro Val
                    325                 330                 335
Glu Glu Gly Arg Cys Phe Glu Leu Leu Phe Asn Asn Gln Val Thr Pro
                340                 345                 350
Ala Ile Phe Asp Lys Lys Pro Leu Leu Lys Asp Val Leu Gly Val Phe
            355                 360                 365
Glu Glu Asn Val Cys Thr Met Asp Ser Leu Glu Ile Ser His Ser Asp
            370                 375                 380
Gln Cys Val His Ile Val Ala Gly Glu Thr Phe Arg Asn Tyr Asp Glu
385                 390                 395                 400
Ile Lys Ala Val Leu Glu Val Ile Leu Asn Glu Pro Asp Ile Leu
                    405                 410                 415
Val Gly Ala Glu Glu Gly Ser Val Ala Asp Tyr Val Lys Ala Gly Lys
                420                 425                 430
His Phe Leu Phe Glu Asn His Gln Trp Val Arg Asn Gly Leu Lys Leu
            435                 440                 445
Ala Lys Gly Leu Ala Glu Pro Gly Gln Arg Ala Lys Asp Asn Thr Asn
    450                 455                 460
Pro Ser Thr Pro Arg Pro Ile Glu Asp Ala Asp Tyr Ile His Pro Phe
465                 470                 475                 480
Asp Asn Gly Gln Pro Leu Pro Gly Arg Ser Asp Gln Trp Val Ser Gly
                485                 490                 495
Phe Glu Val Thr Arg Leu Arg His His Asp Glu Met Pro His Ile Arg
            500                 505                 510
Ser Val Arg Asn Thr Gly Ile His Gly Leu Pro Gly Asp Phe Leu Ser
            515                 520                 525
Asn Tyr Pro Arg Leu Pro Thr Pro Val Phe His Arg Leu Arg Asp Leu
    530                 535                 540
Trp Asp Asp Val Ile Gly Ile Leu Met Lys Leu Glu Phe Gly Asp Asn
545                 550                 555                 560
Cys Ser Pro Val Leu Asn Val Thr Ala Asn Ala Asp Trp Val Arg Ser
                565                 570                 575
Glu Thr Thr Ile Asn Phe Ile Ser Asp Gln Pro Gly Lys Ala Gln Ser
            580                 585                 590
Arg Pro Arg Glu Asp Gly Gly Phe Asp Ile Leu Val Pro Cys Arg Gly
            595                 600                 605
Ile Ala Thr Arg Ser Ile Arg Leu Leu Pro Leu Phe Ile Arg Leu Pro
    610                 615                 620
Asn Arg Phe Arg Ala Val Ala Leu Leu Asn Gly Arg Gln Ser Asp Tyr
625                 630                 635                 640
Asp Asn Tyr Gly Trp Pro Val Phe Asn Pro Val Ile Pro Leu Pro Gln
                645                 650                 655
Met Asp Ser Phe Tyr Val Glu Ala Val Ala Ala Gly Arg Ser Met Tyr
            660                 665                 670
Pro Pro Gly Phe Leu Leu Gly Arg Tyr Asp Ala Leu Glu Tyr Leu Val
            675                 680                 685
```

-continued

| | | | | | | | | | | | | | | |
|---|---|---|---|---|---|---|---|---|---|---|---|---|---|---|
| His | Thr | Ala | Thr | Val | Tyr | Gly | Ala | Glu | Glu | Ala | Phe | Leu | Leu | Pro | Phe |
| 690 | | | | | 695 | | | | | 700 | | | | |
| Thr | His | His | Val | Arg | Val | Tyr | Pro | Pro | Arg | Pro | Gly | Arg | Glu | Ile |
| 705 | | | | | 710 | | | | 715 | | | | | 720 |
| Pro | Phe | Gly | Ser | Trp | Cys | Lys | Asn | Tyr | Lys | Phe | Glu | Ala | Glu | Arg | Phe |
| | | | | 725 | | | | 730 | | | | | 735 | |
| Trp | Tyr | Asp | Ala | Asp | Trp | Lys | Leu | Arg | Val | His | Glu | Thr | Asn | His | Asp |
| | | | 740 | | | | 745 | | | | | 750 | | |
| Phe | Asp | Arg | Leu | Ile | Glu | Ile | Thr | Lys | Thr | Cys | Arg | Arg | Asn | Pro | Pro |
| | | 755 | | | | 760 | | | | | 765 | | | |
| Glu | Glu | Asn | Leu | Gln | Ala | Lys | Leu | Glu | Asp | Thr | Ala | Arg | Lys | Val | Cys |
| 770 | | | | 775 | | | | | 780 | | | | | |
| Ser | Val | Trp | Gln | Tyr | Asn | Ile | Met | Ile | Ala | Ser | Ser | Val | Ala | Phe | Leu |
| 785 | | | | 790 | | | | | 795 | | | | | 800 |
| Val | Pro | Leu | Tyr | Phe | Thr | Leu | Tyr | Val | Pro | Tyr | Leu | Gln | Phe | Tyr | Leu |
| | | | | 805 | | | | | 810 | | | | | 815 |
| His | Val | Asp | Pro | Gly | Asp | Tyr | Ile | Leu | Leu | Pro | Pro | Val | Leu | Trp | Leu |
| | | | 820 | | | | | 825 | | | | | 830 | |
| Val | Trp | Thr | Asn | Leu | Cys | Tyr | Gly | Tyr | Ala | Cys | Asp | Ala | Trp | Cys | Arg |
| | | 835 | | | | | 840 | | | | | 845 | | |
| Leu | Phe | Phe | Phe | Val | Glu | Ala | Gly | Lys | Lys | Glu | Leu | Val | His | Ser |
| 850 | | | | | 855 | | | | | 860 | | | | |
| Ser | Glu | Glu | Phe | Ser | Ser | Asp | Pro | Ser | Ser | Thr | Leu | Leu | Ile | Pro | Thr |
| 865 | | | | | 870 | | | | | 875 | | | | | 880 |
| Met | Gly | Thr | Arg | Gly | Asp | His | Val | Pro | Pro | Arg | Phe | Phe | Ala | Asn | Met |
| | | | | 885 | | | | | 890 | | | | | 895 |
| Ala | Val | Leu | Ala | Gly | Val | Lys | Thr | His | Leu | Leu | Lys | Leu | Gln | Thr | Ala |
| | | | 900 | | | | | 905 | | | | | 910 | |
| Thr | Tyr | Gly | Asp | Leu | Glu | Asn | Leu | Lys | Lys | Gly | Lys | Leu | Gly | Ser | Leu |
| | | 915 | | | | | 920 | | | | | 925 | | |
| Leu | Pro | Gly | Tyr | Leu | Gln | Asn | His | Tyr | Ser | Val | Leu | Arg | Gly | Tyr | Lys |
| | 930 | | | | | 935 | | | | | 940 | | | |
| Ala | Ala | Phe | Thr | Pro | His | Val | Glu | Leu | Asp | Met | Pro | Asn | Ala | Thr | Ser |
| 945 | | | | | 950 | | | | | 955 | | | | | 960 |
| Tyr | Asn | Leu | Ala | Pro | Pro | Arg | Ser | Tyr | Ile | Asn | Lys | Ile | Arg | Tyr | Leu |
| | | | | 965 | | | | 970 | | | | | 975 | |
| Thr | Asp | Glu | Asn | Arg | Ser | Gly | Ala | Ser | Met | Ile | Asp | Arg | Ala | Val | Thr |
| | | | | 980 | | | | 985 | | | | | 990 | |
| Trp | Phe | Ala | Glu | Glu | Leu | Ala | Asp | Thr | Phe | Trp | Pro | Asp | Trp | Gln | Ile |
| | | 995 | | | | | 1000 | | | | | 1005 | | |
| Gly | Cys | Leu | Arg | Gly | Cys | Asn | Leu | Pro | Arg | Ser | Ala | Asp | Gly | Val | Ser |
| | 1010 | | | | | 1015 | | | | | 1020 | | | |
| Leu | Ile | Thr | Lys | Gln | Pro | Asn | Leu | Lys | Thr | Gly | Lys | Ile | Gly | Trp | Leu |
| 1025 | | | | | 1030 | | | | | 1035 | | | | | 1040 |
| His | Gly | Ser | Ala | Asp | Pro | Ala | Val | Val | Pro | Lys | Asp | Ile | Arg | Asp | Lys |
| | | | | 1045 | | | | | 1050 | | | | | 1055 |
| Tyr | Pro | Leu | Val | Pro | Asn | Gly | Asp | His | Asn | Glu | Ile | Phe | Arg | His | Tyr |
| | | | | 1060 | | | | 1065 | | | | | 1070 | |
| Asp | Lys | Ile | Tyr | Met | Pro | Gly | Gly | Ala | Gly | Ala | Val | Gln | Thr | Ala | Ile |
| | | 1075 | | | | | 1080 | | | | | 1085 | | |
| Ala | Cys | Gly | Cys | Glu | Val | Val | Val | Thr | Asp | Val | Asn | Leu | Asp | Arg | Asp |
| | | 1090 | | | | 1095 | | | | | 1100 | | | |
| Tyr | His | Thr | Met | Pro | Thr | Gln | Lys | Asp | Phe | His | Gln | Pro | Ser | Ile | Leu |

```
                1105                      1110                      1115                      1120
        Pro  Tyr  Phe  Ala  Trp  Leu  Trp  Arg  Gln  Gly  Phe  Asp  Val  Lys  Leu  Pro
                          1125                      1130                      1135
        Arg  Val  Leu  Leu  Val  Ile  Gly  Trp  Leu  Lys  Phe  His  Tyr  Ser  Ile  Arg
                          1140                      1145                      1150
        Tyr  Lys  His  Leu  Glu  Phe  Ala  Ala  Asp  Phe  Val  Ile  Arg  Ala  Gly  Leu
                          1155                      1160                      1165
        Phe  Trp  Trp  Tyr  Gly  Cys  Leu  His  Leu  Leu  Pro  Phe  Met  Ala  Ala  Ala
                          1170                      1175                      1180
        Ile  Met  Ala  Pro  Arg  Phe  Val  Lys  Lys  Tyr  Leu  Val  Gly  Met  Ala  Trp
        1185                      1190                      1195                      1200
        Leu  Thr  Glu  Pro  Gly  Leu  Leu  Met  Leu  Lys  Ala  Leu  Trp  Arg  Phe  Pro
                          1205                      1210                      1215
        Ile  Phe  Met  Val  Thr  Pro  Arg  Trp  Met  Leu  Pro  Phe  Ile  Val  Thr  Val
                          1220                      1225                      1230
        Ser  Val  Tyr  Asn  Trp  Trp  Trp  Pro  Leu  Ser  Gln  Asp  Gly  Leu  Asn  Tyr
                          1235                      1240                      1245
        Ala  Ser  Lys  Arg  Phe  Glu  Leu  Ile  Phe  Glu  Pro  Val  Thr  Arg  Gly  Lys
                          1250                      1255                      1260
        His  Thr  Phe  Ser  Tyr  Pro  Phe  Gly  His  Trp  Cys  Leu  Arg  Asp  Thr  Asn
        1265                      1270                      1275                      1280
        Ser  Met  Ile  Val  Tyr  Glu  Gly  Lys  Phe  Val  Asn  Pro  Ser  Glu  Thr  Ser
                          1285                      1290                      1295
        Ile  Gly  Ser  Pro  Phe  Lys  Leu  Ser  Lys  Ser  Val  Arg  Pro  Val  Arg  Pro
                          1300                      1305                      1310
        Gly  Ala  Val  Phe  His  Leu  Val  Pro  Phe  His  Val  Gln  Lys  Leu  Leu  Asp
                          1315                      1320                      1325
        Ser  Met  Asp  Glu  Ala  Pro  Leu  Pro  Tyr  Ser  Ala  Asn  His  Asn  Cys  Thr
                          1330                      1335                      1340
        Thr  Val  Ile  Leu  Lys  Gly  Ile  Met  Tyr  Arg  Ser  Ala  Leu  Gly  Phe  Val
        1345                      1350                      1355                      1360
        Phe  Ala  Tyr  Met  Val  Ser  Trp  Ala  Val  Tyr  Leu  Val  Leu  Arg  Pro  Pro
                          1365                      1370                      1375
        Gln  Ala  Ala  Ala  Thr  Val  Tyr  His  Trp  Val  Tyr  Pro  Glu  Arg  Ser  Trp
                          1380                      1385                      1390
        Asp  Thr  Ser  Arg  Leu  Tyr  His  Leu  Leu  Leu  Gly  Phe  Ala  Ala  Gly  Gly
                          1395                      1400                      1405
        Thr  Val  Pro  Met  Glu  Val  Ile  Asp  Glu  Glu  His  Val  Glu  Glu  Lys  Pro
                          1410                      1415                      1420
        Ser  Val  Ala  Gly  Gln  Ser  Glu  Pro  Ala  Ala  Glu  Ile  Asp  Asn  Asp  Lys
        1425                      1430                      1435                      1440
        Ile  Ser  Asp  Tyr  Asp  Gln  Glu  Trp  Trp  Gly  Ser  Gln  Asp  Ser  Ile  Asp
                          1445                      1450                      1455
        Thr  Val  Val  Asn  Asp  Leu  Cys  Tyr  Leu  Leu  Ser  Phe  Leu  Lys  Asp  Thr
                          1460                      1465                      1470
        Ala  Ile  Pro  Glu  Glu  Val  Lys  Leu  Asp  Val  Val  Glu  Leu  Ala  Tyr  Thr
                          1475                      1480                      1485
        Gln  Leu  Val  Gln  Asp  Glu  Lys  Glu  Arg  Ile  Pro  Glu  Pro  Lys  Gly  Thr
                          1490                      1495                      1500
        Lys  Ile  Leu  Asp  Met  Pro  Asn  Trp  Lys  Pro  Gly  Asn  Trp  Ala  Lys  Leu
        1505                      1510                      1515                      1520
        Ile  Asp  Glu  Thr  His  Arg  Val  Leu  Ser  Gln  Phe  Thr  Gln  Tyr  Thr  Pro
                          1525                      1530                      1535
```

```
Arg Val Leu Asn Glu Leu Val Val Trp Leu Lys Gly Leu Gly Glu Asn
            1540                1545                1550
Leu Tyr Arg Val Ala Glu Pro Ile Leu Met Leu Leu Val Arg Ala Met
        1555                1560                1565
Arg Ala Lys Ser Val Ser Asp Arg Ala Thr Arg Ser Val Tyr His
    1570                1575                1580
Cys Leu Cys His Trp Leu Asp Val Met Tyr Gly Gly Ser Ala Pro Thr
1585            1590                1595                    1600
Arg Val Lys Thr Val Trp Gly Leu Thr Gly Leu Val Ala Ser Gly Met
            1605                1610                1615
Thr Ser Gln Lys Ala Ile Leu Ala Gln Asn Ile Ala Met Met Glu Tyr
            1620                1625                1630
Gln Gly Arg Gly Asn Phe Leu Asp Asp Tyr Asp Asn Phe Val Ser Asn
            1635                1640                1645
Ile Lys Glu Pro Gly Lys Gly Leu Pro Gly Ile Asn Thr Ile Gly Gly
        1650                1655                1660
Pro Gln Arg Arg Pro Ile Arg Tyr Lys Asn Pro Val Met Ser His Gln
1665            1670                1675                1680
Ala Ala Glu Ile Cys Gly Leu Lys Pro Gly Glu Tyr Glu Val Asp Asp
                1685                1690                1695
Arg Tyr Gln Glu Arg Ile Asn Asp Tyr Leu Ala Glu Gly Ile Pro Gln
            1700                1705                1710
Ala Val Asp Gly Val Leu Phe Gly Asp Arg Asn Pro Asp Arg Ile Ala
            1715                1720                1725
Arg Ser Ile Ser Arg Tyr Glu Pro Glu Tyr Ser Gly Cys Ser Pro Glu
        1730                1735                1740
Asp Lys Ala Leu Val Glu Asp Thr Ala Arg Ala Met Phe Glu Gln Trp
1745            1750                1755                    1760
Pro Glu Val Phe Ala Asp Arg Asp Ile Met Leu Pro Lys Gly Val Glu
                1765                1770                1775
Leu Tyr Ile Lys Glu Lys Tyr Ser Ala Gly Thr Pro Phe Ile Ser Ser
            1780                1785                1790
Phe Tyr Lys Ser Arg Lys Ala Leu Lys Gln Ala Gly Val Met Asp Val
            1795                1800                1805
Ile Arg Lys Asn Ala Leu Glu Cys Ile Ser Thr Gly Lys Tyr Pro Thr
        1810                1815                1820
Gln Phe Tyr His Ala Phe Ala Lys Ser Gln Ala Val Pro Gly Gln Pro
1825            1830                1835                    1840
Leu Leu Ala Pro Arg Met Lys Asp Leu Arg Thr Val Val Ser Glu Asp
                1845                1850                1855
Leu Ser Ala Tyr Met Val Asp Gln Ile Phe Gln Ile Glu Ala Asn Lys
            1860                1865                1870
Arg Ile Thr Trp Glu Thr Tyr Gly Ala Gly Ser Gly Met Pro Leu Ser
        1875                1880                1885
Gln Ser Met Ala Arg Ile Trp Asp Glu Leu His Asp Leu Arg Lys Arg
    1890                1895                1900
Glu Gly Gly Gln Phe Ile Ile Ala Asp Ala Thr Ala Tyr Asp Ser Asn
        1905                1910                1915                1920
Cys Lys Pro Ala Leu Phe His Gly Ala Gly Lys Leu Val Glu Leu Gly
                1925                1930                1935
Phe Gln Asn His Pro Ser Gly Lys Gly Arg Gln Phe Ala Gln Val Val
                1940                1945                1950
Gln Cys Lys Phe Glu Ala Met Gln Asn Ala Trp Val Met Gly Ile Thr
            1955                1960                1965
```

```
Glu  Pro  Ser  Tyr  Thr  Ala  Leu  Thr  Phe  His  Val  Pro  Asp  Val  Ala  Val
     1970                1975                1980

Arg  His  Glu  Leu  Glu  Ser  Lys  Tyr  Pro  Ala  His  Phe  Ala  Thr  Phe  Ser
1985                1990                1995                               2000

Glu  Leu  Leu  Ala  His  Asn  Asn  Val  Asn  Val  Thr  Glu  Trp  Lys  Arg  Leu
               2005                2010                2015

Ser  Trp  Glu  Glu  Arg  Lys  Ala  Cys  Ala  Arg  Asp  Met  Gln  Ala  Val  Pro
          2020                2025                2030

Gly  Lys  Val  Phe  Leu  Thr  Asn  Asp  Pro  Ala  Leu  Arg  Leu  Gln  Gly  Ser
          2035                2040                2045

Ser  Trp  Gln  Gly  Ser  Phe  Thr  Thr  Glu  Pro  Lys  Arg  Asp  Glu  Phe  Arg
     2050                2055                2060

Lys  Tyr  Gln  Thr  Tyr  Phe  Tyr  Asp  Ser  Lys  Ala  Ala  Met  Arg  Glu  Asp
2065                2070                2075                               2080

Ile  Lys  Arg  Ile  Val  Phe  Ala  Asn  Arg  Glu  Val  Ile  Ser  Asn  Val  His
               2085                2090                2095

His  Lys  Asn  Arg  Gly  Gly  Gly  Thr  Gly  Gln  Ser  Ala  Thr  Ser  Trp  Asp
               2100                2105                2110

Asn  Thr  Ala  Thr  Phe  Lys  Leu  Gly  Val  Ile  Ser  Ala  Trp  Ala  Arg  Ala
          2115                2120                2125

Thr  Gly  Lys  Pro  Pro  Lys  Asp  Phe  Phe  Cys  Ser  Asn  Arg  Leu  Tyr  Asn
          2130                2135                2140

Thr  Ser  Asp  Asp  Thr  Val  Trp  Trp  Ser  Lys  Asp  Leu  Leu  Ser  Ser  Ala
2145                2150                2155                               2160

Glu  Val  Asp  Arg  Phe  Lys  Gln  Ala  Ala  Asp  Phe  Gly  Ile  Leu  Leu
               2165                2170                2175

Glu  Ile  Gly  Ser  Thr  Lys  Lys  Ile  Thr  Glu  Val  Glu  Tyr  Leu  Ser  Lys
               2180                2185                2190

Leu  Pro  Arg  Arg  Pro  Thr  Ala  Glu  Asp  Ser  Ala  Asp  Tyr  Arg  Ala  Trp
               2195                2200                2205

Arg  Gln  Gly  Arg  Ile  Glu  Asn  Met  Arg  Ser  Ser  Gly  Arg  Phe  Ser  Glu
          2210                2215                2220

Glu  Gln  Leu  Leu  Ser  Ile  Glu  Arg  Glu  Gln  Leu  Pro  Gln  Phe  Leu  Met
2225                2230                2235                               2240

Val  Gln  Asn  Pro  Thr  Ala  Ile  Leu  Met  Arg  Arg  Thr  Ala  Phe  Arg  Tyr
               2245                2250                2255

Tyr  Gln  Ser  Ser  Pro  Ser  Lys  Phe  Leu  Tyr  Thr  Ser  Cys  Glu  Arg  Gly
               2260                2265                2270

Ala  Gly  His  Ala  Leu  Val  Thr  Ala  Phe  Gln  Pro  Ala  Leu  Tyr  Lys  Arg
          2275                2280                2285

Phe  Ala  Ile  Glu  Tyr  Ala  Glu  Asp  Leu  Asn  Arg  Leu  Cys  Lys  Glu  His
     2290                2295                2300

His  Ile  Asn  Gln  Arg  Tyr  Glu  Leu  Val  Ser  Gln  Gln  Asp  Arg  Met  Lys
2305                2310                2315                               2320

Met  Gln  Val  Ile  Asn  Val  Asn  Pro  Asn  Trp  Lys  Arg  Asn  Phe  Lys  Leu
               2325                2330                2335

Ser  Pro  Arg  Gln  Glu  Ala  Phe  Leu  Arg  Trp  Ile  Arg  Gln  Ala  Lys  Phe
          2340                2345                2350

Pro  Ser  Tyr  Arg  Gln  Val  Leu  Asp  Ile  His  Leu  Arg  Ile  Arg  Asp  Pro
          2355                2360                2365

Asp  Pro  Ser  Ala  His  Asp  Arg  Phe  Ile  Ala  Lys  Leu  Asp  Arg  Ala  Trp
          2370                2375                2380

Arg  Asn  Pro  Asp  Glu  Gly  Ile  Arg  Asp  Ile  Val  Asp  Gly  Val  Tyr  Arg
```

```
                2385                    2390                    2395                    2400

Tyr  Thr  Asp  Met  Ile  Pro  Glu  Glu  Phe  Lys  Arg  Phe  Met  Pro  Ser  Thr
                           2405                    2410                    2415

Asp  Met  Leu  Tyr  Ala  Glu  Asn  Pro  Trp  His  Thr  His  Asn  Gln  Tyr  Val
                           2420                    2425                    2430

Glu  Lys  Phe  Ile  Tyr  Leu  Lys  Leu  Leu  Glu  Thr  Thr  Thr  Val  Asp  Glu
                           2435                    2440                    2445

Leu  Thr  Phe  Ala  Gln  Phe  Asp  Ala  Val  Ala  Lys  Glu  Ser  Pro  Tyr  Gly
                           2450                    2455                    2460

Ile  Cys  Met  Asn  Thr  Ile  Lys  Phe  Trp  Glu  Asp  Leu  Arg  Asp  Pro  Asp
       2465                    2470                    2475                    2480

Tyr  Leu  Lys  Asp  Leu  Leu  Ala  Ser  Glu  Ala  Met  Ile  Asp  Lys  Val  Arg
                           2485                    2490                    2495

Ile  Tyr  Gln  Gly  Met  Thr  Val  Ile  Ile  Ser  Ala  Met  Tyr  Phe  Ala  Met
                           2500                    2505                    2510

His  Trp  Val  Glu  Leu  Phe  Ile  Gln  Ser  Leu  Phe  Leu  Ile  Gly  Pro  Leu
                           2515                    2520                    2525

Tyr  Asn  Leu  Phe  Met  Trp  Ser  Phe  Trp  Gly  Leu  Ser  Lys  Val  Tyr  Gly
                           2530                    2535                    2540

Leu  Ala  Asn  Thr  Phe  Tyr  Trp  His  Gly  Lys  Ala  Arg  Ser  Ser  Arg  Glu
       2545                    2550                    2555                    2560

Ile  Ser  Ser  Ile  Leu  Pro  Arg  Asp  Pro  Tyr  Met  Trp  Ser  Lys  Arg  Phe
                           2565                    2570                    2575

Val  Ser  Thr  Met  Ala  Asp  Phe  Ile  Pro  Glu  Arg  Phe  Ala  Leu  Gly  Ile
                           2580                    2585                    2590

Val  Pro  Val  Thr  Leu  Val  Leu  Asp  Gly  Leu  Ala  Glu  Ile  Ile  Glu  Val
                           2595                    2600                    2605

Leu  Phe  Gly  Arg  Met  Trp  Arg  Leu  Phe  Ala  Asn  Leu  Lys  Ser  Val  Gly
                           2610                    2615                    2620

Thr  Asp  Phe  Ser  Asp  Ala  Arg  Ser  Gly  Lys  Ser  Leu  Asn  Val  Pro  Ser
       2625                    2630                    2635                    2640

Asn  Pro  Trp  Ala  Ala  Tyr  Ala  His  Thr  Tyr  Ala  Thr  Lys  Ala  Ile  Glu
                           2645                    2650                    2655

His  Gly  His  Val  Thr  Val  Ala  Ala  Lys  Thr  Ala  Ser  Gly  Lys  Ser  Thr
                           2660                    2665                    2670

Phe  Phe  Pro  Ala  Ala  Val  Trp  Ala  Glu  Arg  Arg  Asn  Ile  Gly  Ile  Lys
                           2675                    2680                    2685

Lys  Leu  Trp  Ile  Val  Met  Pro  Arg  Lys  Ile  Leu  Arg  Asp  Asn  Trp  Glu
                           2690                    2695                    2700

Ile  Pro  Phe  Asp  Ile  Arg  Ser  Gln  Ile  Val  Lys  Arg  Gly  Lys  Thr  Leu
       2705                    2710                    2715                    2720

Asp  Pro  Ser  Ala  Asp  Ile  Tyr  Val  Thr  Thr  Tyr  Gly  His  Phe  Arg  Thr
                           2725                    2730                    2735

Arg  Ile  Gly  Gly  Leu  Val  Pro  Arg  Asp  Asn  Leu  Val  Phe  Phe  Asp  Glu
                           2740                    2745                    2750

Phe  His  Glu  Met  Asp  Gly  Phe  Met  Leu  Gln  Asp  Val  Glu  Asp  Trp  Lys
                           2755                    2760                    2765

Gly  Pro  Thr  Ile  Phe  Met  Ser  Ala  Thr  Pro  Val  Ala  Leu  His  Gly  Met
                           2770                    2775                    2780

Ala  Gly  Ile  Pro  Phe  Leu  Glu  Pro  Thr  Leu  Pro  Lys  Arg  Phe  Asn  Leu
       2785                    2790                    2795                    2800

Thr  Val  Tyr  Lys  Val  Asp  Ser  Asp  Asp  Val  Leu  Glu  Met  Trp  Asn  Arg
                           2805                    2810                    2815
```

```
Ala Arg Asn Gln Phe Ala Asp Gln Pro Glu Leu Leu Ala Arg Pro Met
            2820                2825                2830

Ile Ile Val Pro Thr Tyr Asn Glu Leu Lys Lys Thr Ile Ala Gly Leu
        2835                2840                2845

Glu Asn Leu Asp Arg Ser Ile Thr Trp His Glu Val Ser Ser Asn Ser
    2850                2855                2860

Pro Leu Val Pro Lys Thr Gly Gly Leu Val Cys Thr Pro Tyr Val Gln
2865                2870                2875                2880

Thr Gly Ile Asp Ile Lys Pro Ala Pro Ser Ile Leu Ile Asp Ser Gly
                2885                2890                2895

Arg Asp Val Ile Val His Lys Gly Arg Leu Val Thr Pro His Pro Tyr
            2900                2905                2910

Thr Asp Glu Lys Thr Asn Glu Gln Arg Val Asn Arg Val Gly Arg Thr
    2915                2920                2925

Met Asp Gly Val Val Ile Gln Pro Gln Leu Ala Gly Thr Gly Asn Pro
    2930                2935                2940

Pro Val Lys Tyr Pro Ser Gly Ile Phe Phe Ser Ser Glu Leu Val Ala
2945                2950                2955                2960

Gly Gln Tyr Lys Val Pro Arg Leu Thr Lys Val Asn Gly Cys Val His
            2965                2970                2975

Pro Glu Leu Pro Tyr Met Ser Ile Lys Tyr Thr Ser Glu Leu Ser Asp
            2980                2985                2990

Pro Ala Lys Ala Arg Glu Glu Glu Gln Ser Val Thr Lys Ser Leu Leu
    2995                3000                3005

Phe Ile His Leu Met Ala Leu Ala Gly Val Arg Gln Ser Glu Trp Ala
    3010                3015                3020

Leu Arg Tyr Asn Arg Tyr Phe Glu Leu His Leu Pro Phe Gly Glu Asp
3025                3030                3035                3040

Glu Asp His Leu Glu Arg Ile Leu Thr Ser Gly Lys Leu Arg Tyr Ala
            3045                3050                3055

Asn His Ile Pro Val Asp Met Ala Met Gln Leu Leu Gly Asn Gly His
            3060                3065                3070

Val Thr Trp Gly Ile Gly Gly Val Pro Thr Ile Thr Arg Pro Arg Tyr
        3075                3080                3085

Pro Cys Asp Gly Met Trp Val Glu Asp Pro Ser Ser Arg Lys Ser Tyr
        3090                3095                3100

Ala His Lys Val Leu Leu His Gln Arg Glu His Ala Glu Ile Gly Met
3105                3110                3115                3120

Trp Gln Ala Gln Val Asn Glu Leu Arg Ala Gln Asn Leu Ala Leu Gln
                3125                3130                3135

Ser Gln Leu Arg Ser Ala Cys Thr Arg Arg Ser Thr Ala Gly Arg Ile
            3140                3145                3150

Leu Arg His Thr Arg Pro Pro Asp Ile Pro Val Cys Gly
            3155                3160                3165
```